(12) United States Patent
Breitenbach et al.

(10) Patent No.: US 9,186,335 B2
(45) Date of Patent: Nov. 17, 2015

(54) HOT MELT TTS FOR ADMINISTERING ROTIGOTINE

(75) Inventors: Armin Breitenbach, Monheim (DE); Hans-Michael Wolff, Monheim (DE)

(73) Assignee: UCB PHARMA GMBH, Monheim (DE)

( * ) Notice: Subject to any disclaimer, the term of this patent is extended or adjusted under 35 U.S.C. 154(b) by 929 days.

(21) Appl. No.: 10/523,908

(22) PCT Filed: Jul. 29, 2003

(86) PCT No.: PCT/EP03/08348
§ 371 (c)(1),
(2), (4) Date: Jan. 28, 2005

(87) PCT Pub. No.: WO2004/012721
PCT Pub. Date: Feb. 12, 2004

(65) Prior Publication Data
US 2005/0260254 A1 Nov. 24, 2005

(30) Foreign Application Priority Data
Jul. 30, 2002 (DE) .................................. 102 34 673

(51) Int. Cl.
*A61K 9/50* (2006.01)
*A61K 9/70* (2006.01)
*A61K 31/381* (2006.01)

(52) U.S. Cl.
CPC ............. *A61K 9/7069* (2013.01); *A61K 31/381* (2013.01)

(58) Field of Classification Search
None
See application file for complete search history.

(56) References Cited

U.S. PATENT DOCUMENTS

| | | | |
|---|---|---|---|
| 4,144,317 A | 3/1979 | Higuchi et al. ................ 424/21 |
| 4,863,970 A | 9/1989 | Patel et al. .................... 514/772 |
| 4,880,633 A | 11/1989 | Loper et al. ................... 424/449 |
| 4,915,950 A | 4/1990 | Miranda et al. ............... 424/448 |
| 4,973,468 A | 11/1990 | Chiang et al. ................. 424/449 |
| 5,043,482 A | 8/1991 | Maignan et al. .............. 568/734 |
| 5,069,909 A | 12/1991 | Sharma et al. ................ 424/449 |
| 5,091,186 A | 2/1992 | Miranda et al. ............... 424/448 |
| 5,124,157 A | 6/1992 | Colley et al. .................. 424/448 |
| 5,147,916 A | 9/1992 | Sweet ............................ 524/266 |
| 5,177,112 A | 1/1993 | Horn .............................. 514/65 |
| 5,225,198 A | 7/1993 | Sharma et al. ................ 424/443 |
| 5,234,690 A | 8/1993 | Chiang et al. ................. 424/448 |
| 5,246,997 A | 9/1993 | Sweet |
| 5,252,334 A | 10/1993 | Chiang et al. ................. 424/448 |
| 5,252,335 A | 10/1993 | Chiang ......................... 424/449 |
| 5,271,940 A | 12/1993 | Cleary et al. .................. 424/448 |
| 5,273,755 A | 12/1993 | Venktraman et al. ......... 424/448 |
| 5,273,756 A | 12/1993 | Fallon et al. .................. 424/448 |
| 5,273,757 A | 12/1993 | Jaeger et al. .................. 424/448 |
| 5,300,299 A | 4/1994 | Sweet et al. |
| 5,308,625 A | 5/1994 | Wong et al. ................... 424/449 |
| 5,382,596 A | 1/1995 | Sleevi et al. .................. 514/459 |
| 5,393,529 A | 2/1995 | Hoffmann et al. ............ 424/445 |
| 5,456,745 A | 10/1995 | Roreger et al. ............... 106/128 |
| 5,527,536 A | 6/1996 | Merkle et al. ................. 424/448 |
| 5,554,381 A | 9/1996 | Roos et al. .................... 424/449 |
| 5,559,165 A | 9/1996 | Paul .............................. 523/111 |
| 5,601,839 A | 2/1997 | Quan et al. .................... 424/448 |
| RE35,474 E | 3/1997 | Woodard et al. |
| 5,658,975 A * | 8/1997 | Ulman et al. .................. 524/266 |
| 5,670,164 A | 9/1997 | Meconi et al. ................ 424/448 |
| 5,688,524 A | 11/1997 | Hsu et al. ...................... 424/449 |
| 5,733,571 A | 3/1998 | Sackler ......................... 424/449 |
| 5,771,890 A | 6/1998 | Tamada ......................... 128/635 |
| 5,807,570 A | 9/1998 | Chen et al. .................... 424/449 |
| 5,834,010 A | 11/1998 | Quan et al. .................... 424/448 |
| 5,840,336 A | 11/1998 | Hsu et al. ...................... 424/484 |
| 5,843,472 A | 12/1998 | Ma et al. ....................... 424/449 |
| 5,876,746 A | 3/1999 | Jona et al. ..................... 424/449 |
| 5,879,701 A | 3/1999 | Aduett et al. ................. 424/448 |
| 5,891,461 A | 4/1999 | Jona et al. ..................... 424/449 |
| 5,902,603 A | 5/1999 | Chen et al. .................... 424/449 |
| 5,906,830 A | 5/1999 | Farinas et al. ................ 424/448 |
| 5,980,932 A | 11/1999 | Chiang et al. |
| 6,024,974 A | 2/2000 | Li .................................. 424/448 |
| 6,024,976 A | 2/2000 | Miranda et al. ............... 424/449 |
| 6,063,398 A | 5/2000 | Gueret .......................... 424/443 |
| RE36,754 E * | 6/2000 | Noel .............................. 424/449 |
| 6,218,421 B1 | 4/2001 | King ............................. 514/421 |
| 6,316,022 B1 | 11/2001 | Mantelle et al. .............. 424/448 |
| 6,372,920 B1 | 4/2002 | Minaskanian et al. ......... 549/75 |
| 6,393,318 B1 | 5/2002 | Conn et al. .................... 604/20 |
| 6,398,562 B1 | 6/2002 | Butler et al. ................... 439/91 |
| 6,465,004 B1 | 10/2002 | Rossi-Montero et al. .... 424/448 |
| 6,620,429 B1 * | 9/2003 | Muller .......................... 424/449 |
| 6,685,959 B1 | 2/2004 | Moreau et al. ................ 424/449 |
| 6,687,522 B2 | 2/2004 | Tamada ......................... 600/347 |

(Continued)

FOREIGN PATENT DOCUMENTS

CA 2 327 187 A1 11/1999
CA 2 532 804 2/2005

(Continued)

OTHER PUBLICATIONS

Blindauer (2003) Arch. Neurol. 60(12): 1721-1728.

(Continued)

*Primary Examiner* — Hasan Ahmed

(74) *Attorney, Agent, or Firm* — Harness, Dickey & Pierce P.L.C.

(57) ABSTRACT

The invention relates to a transdermal therapeutic system (TTS) which contains a rotigotine-containing adhesive layer and is characterized by the fact that the adhesive layer contains a hot-meltable contact adhesive. The invention also relates to the use of rotigotine for producing the adhesive layer of a TTS in a hot melt method, and a method for producing such a TTS.

22 Claims, 18 Drawing Sheets

(56) References Cited

U.S. PATENT DOCUMENTS

| | | | |
|---|---|---|---|
| 6,699,498 B1 | 3/2004 | Müller | 424/449 |
| 6,884,434 B1 | 4/2005 | Muller et al. | 424/487 |
| 6,899,894 B1 | 5/2005 | Klein et al. | 424/448 |
| 7,309,497 B2 | 12/2007 | Rimpler et al. | 424/422 |
| 7,413,747 B2 | 8/2008 | Mueller et al. | 424/448 |
| 8,211,462 B2* | 7/2012 | Breitenbach et al. | 424/449 |
| 2002/0110585 A1 | 8/2002 | Godbey et al. | 424/449 |
| 2003/0026830 A1 | 2/2003 | Lauterback et al. | 424/449 |
| 2003/0027793 A1 | 2/2003 | Lauterback et al. | 514/63 |
| 2003/0166709 A1 | 9/2003 | Rimpler et al. | 514/447 |
| 2004/0034083 A1 | 2/2004 | Stephenson et al. | 514/406 |
| 2004/0048779 A1 | 3/2004 | Schollmayer | 514/2 |
| 2004/0057985 A1 | 3/2004 | Bracht | |
| 2004/0081683 A1 | 4/2004 | Schacht et al. | 424/449 |
| 2004/0110673 A1 | 6/2004 | Steinkasserer et al. | 514/12 |
| 2004/0116537 A1 | 6/2004 | Li et al. | 514/663 |
| 2004/0137045 A1 | 7/2004 | Breitenbach et al. | 424/449 |
| 2004/0209861 A1 | 10/2004 | Benavides et al. | 514/210.01 |
| 2005/0033065 A1 | 2/2005 | Mueller et al. | 549/449 |
| 2005/0048104 A1 | 3/2005 | Venkatraman et al. | |
| 2005/0079206 A1 | 4/2005 | Schacht et al. | 424/449 |
| 2005/0136101 A1 | 6/2005 | Berthold | 424/448 |
| 2005/0175678 A1 | 8/2005 | Breitenbach | 424/448 |
| 2005/0197385 A1 | 9/2005 | Scheller et al. | 514/438 |
| 2005/0260254 A1 | 11/2005 | Breitenbach et al. | 424/449 |
| 2006/0216336 A1 | 9/2006 | Wolff | |
| 2006/0222691 A1 | 10/2006 | Cantor et al. | 424/448 |
| 2006/0263419 A1 | 11/2006 | Wolff | 424/448 |
| 2007/0072917 A1 | 3/2007 | Scheller et al. | 514/357 |
| 2007/0093546 A1 | 4/2007 | Scheller et al. | 514/447 |
| 2007/0191308 A1 | 8/2007 | Kramer | 514/60 |
| 2007/0191470 A1 | 8/2007 | Scheller | 514/438 |
| 2007/0197480 A1 | 8/2007 | Scheller et al. | 514/114 |
| 2008/0008748 A1 | 1/2008 | Beyreuther et al. | 424/449 |
| 2008/0138389 A1 | 6/2008 | Muller et al. | 424/448 |
| 2008/0146622 A1 | 6/2008 | Scheller et al. | 514/357 |
| 2008/0274061 A1 | 11/2008 | Schollmayer et al. | 424/45 |
| 2009/0143460 A1 | 6/2009 | Wolff et al. | 514/438 |
| 2010/0311806 A1 | 12/2010 | Wolff et al. | |
| 2011/0104281 A1 | 5/2011 | Beyreuther et al. | |
| 2011/0165247 A1 | 7/2011 | Breitenbach | |
| 2012/0101146 A1 | 4/2012 | Bouwstra et al. | |
| 2012/0215185 A1 | 8/2012 | Schacht et al. | |
| 2012/0322845 A1 | 12/2012 | Wolff et al. | |

FOREIGN PATENT DOCUMENTS

| | | |
|---|---|---|
| CA | 2 532 859 | 2/2005 |
| CA | 2 547 820 | 6/2005 |
| CA | 2 546 797 | 7/2005 |
| DE | WO 99/49852 A1 | 10/1999 |
| DE | 198 14 083 C2 | 2/2002 |
| DE | 199 58 554 A1 | 6/2002 |
| DE | 199 58 554 C2 | 6/2002 |
| EP | 0 305 756 A1 | 3/1989 |
| EP | 0 360 467 | 3/1990 |
| EP | 0 180 377 | 1/1991 |
| EP | 0 524 775 A1 | 1/1993 |
| EP | 0 663 431 | 7/1995 |
| EP | 0 835 136 | 12/1996 |
| EP | 1 256 340 A1 | 11/2002 |
| JP | 05-208907 B2 | 6/2013 |
| WO | WO 93/07842 | 4/1993 |
| WO | WO 93/14727 | 8/1993 |
| WO | WO 93/16073 | 8/1993 |
| WO | WO 94/04109 | 3/1994 |
| WO | WO 94/07468 | 4/1994 |
| WO | WO 95/00122 | 1/1995 |
| WO | WO 95/01767 | 1/1995 |
| WO | WO 95/05137 | 2/1995 |
| WO | WO 95/05138 | 2/1995 |
| WO | WO 95/24776 | 9/1995 |
| WO | WO 96/39136 | 12/1995 |
| WO | WO 96/00110 | 1/1996 |
| WO | WO 96/22083 | 7/1996 |
| WO | WO 96/22084 | 7/1996 |
| WO | WO 96/40087 | 12/1996 |
| WO | WO 97/09971 | 3/1997 |
| WO | WO 97/11696 | 4/1997 |
| WO | WO 97/29735 | 8/1997 |

OTHER PUBLICATIONS

Chiang, et al. (1995) Proc. Int. Symp. Controlled Release Bioact. Mater. 22, 710-711.
den Daas et al. (1990) Naunyn-Schmiedegerg's Pharmacol. 342: 655-659.
Hsu et al. (1992) Cygnus Therapeutic Systems Project Report N-0923, 2-19.
Levien et al. (2005) Advances in Pharmacy 3(1): 62-92.
LeWitt et al. (2005) Adjunctive Treatment of Advanced Parkinson's Disease with Rotigotine Transdermal System (Prefer Study), manuscript (25 pp).
Loschman et al. (1989) Eur. J. Pharmacol. 373-380.
Pfister (1988) Drug and Cosmetic Ind. (Oct): 44-52.
Pfister (1989) Pharm. Tech. (March): 126-138.
Pfister and Hsieh (1990) Pharm. Tech. (Sept): 132-140.
Pfister and Hsieh (1990) Pharm. Tech. (Oct): 54-60.
Pfister et al. (1991) Chemistry in Britain (Jan): 43-46.
Pfister et al. (1992) Pharm. Tech. (Jan): 42-58 and 83.
Roy et al. (1996) J. Pharn. Science 85(5): 491-495.
Swart et al. (1992) Internatl. J. of Pharmaceutics 88: 165-170.
Thomas et al. (1991) STP Pharma Sci 1(1): 38-46.
Van der Weide, et al. (1988) "The enantiomers of the D-2 dopamine receptor agonist N-0437 discriminate between pre- and postsynaptic dopamine receptors." Eur J Pharmacol 146:319-326.
European Public Assessment Report of the European Medicines Agency (EMEA, 2006) for Neupro® transdermal rotigotine (www.emea.europa.eu/humandocs/PDFs/EPAR/neupro/062606en6.pdf).
Jankovic & Tolosa, *Parkinson's Disease and Movement Disorders*, 5th ed., Philadelphia: Lippincott, p. 121-122, 2006.
Metman et al., *Clinical Neuropharmacology*, 2001, 24:163-169.
Office Action dated Oct. 5, 2007 for U.S. Appl. No. 10/630,633.
Office Action dated Jun. 24, 2008 for U.S. Appl. No. 10/630,633.
Office Action dated Oct. 16, 2008 for U.S. Appl. No. 10/630,633.
Office Action dated Mar. 19, 2009 for U.S. Appl. No. 10/630,633.
Office Action, dated Jul. 28, 2009 issued in U.S. Appl. No. 10/630,633.
Office Action, dated Dec. 24, 2009 issued in U.S. Appl. No. 10/630,633.
Krishna, P., et al. (2010) "A stability indicating of rotigotine in bulk drugs by HPLC assay method", *Research Journal of Pharmaceutical, Biological and Chemical Sciences*, 1(4): 848-857.
LeWitt, P., et al. (2007), "Advanced Parkinson disease treated with rotigotine transdermal system", *Neurology*, 68: 1262-1267.
The Merck Index, http://www.medicinescomplete.com/mc/merck/2010/10253.htm (printed Aug. 18, 2011).
Tanojo H., et al. (1997), "New design of a flow-through permeation cell for studying in vitro permeation studying in vitro permeation studies across biologicai membranes", *Journal of Controlled Release*, 45: 41-47.
Organic Chemistry Reactions, http://www.organic-chemistry.org/namedreactions/cope-elimination.shtm (printed Aug. 24, 2011).
Office Action dated Apr. 15, 2002 issued in U.S. Appl. No. 09/647,290.
Office Action dated Nov. 1, 2002 issued in U.S. Appl. No. 09/647,290.
Office Action dated Aug. 17, 2007 issued in U.S. Appl. No. 10/623,864.
Office Action dated Sep. 13, 2007 issued in U.S. Appl. No. 10/936,620.
Office Action dated May 1, 2008 issued in U.S. Appl. No. 10/936,620.
Office Action dated Sep. 10, 2008 issued in U.S. Appl. No. 10/429,283.
Office Action dated Jan. 26, 2009 issued in U.S. Appl. No. 10/936,020.

(56) References Cited

OTHER PUBLICATIONS

Office Action dated Mar. 30, 2009 issaad in U.S. Appl. No. 10/429,283.
Office Action dated Aug. 18, 2009 issued in U.S. Appl. No. 10/627,990.
Office Action dated Oct. 15, 2009 issued in U.S. Appl. No. 10/139,894.
Office Action dated Nov. 6, 2009 issued in U.S. Appl. No. 10/936,620.
Office Action dated Dec. 23, 2009 issued in U.S. Appl. No. 10/429,283.
Office Action dated Jul. 7, 2010 issued in U.S. Appl. No. 10/630,633.
Office Action dated Oct. 1, 2010 issued U.S. Appl. No. 10/429,283.
Office Action dated Oct. 8, 2010 issued in U.S. Appl. No. 10/936,620.
Office Action dated May 4, 2011 issued in U.S. Appl. No. 10/429,283.
Office Action dated Jun. 13, 2011 issued in U.S. Appl. No. 10/936,620.
Office Action dated Jul. 28, 2011 issued in U.S. Appl. No. 10/630,633.
Office Action dated Feb. 3, 2012 issued in U.S. Appl. No. 10/429,283.
Office Action dated May 3, 2013 issued in U.S. Appl. No. 10/429,283.

* cited by examiner

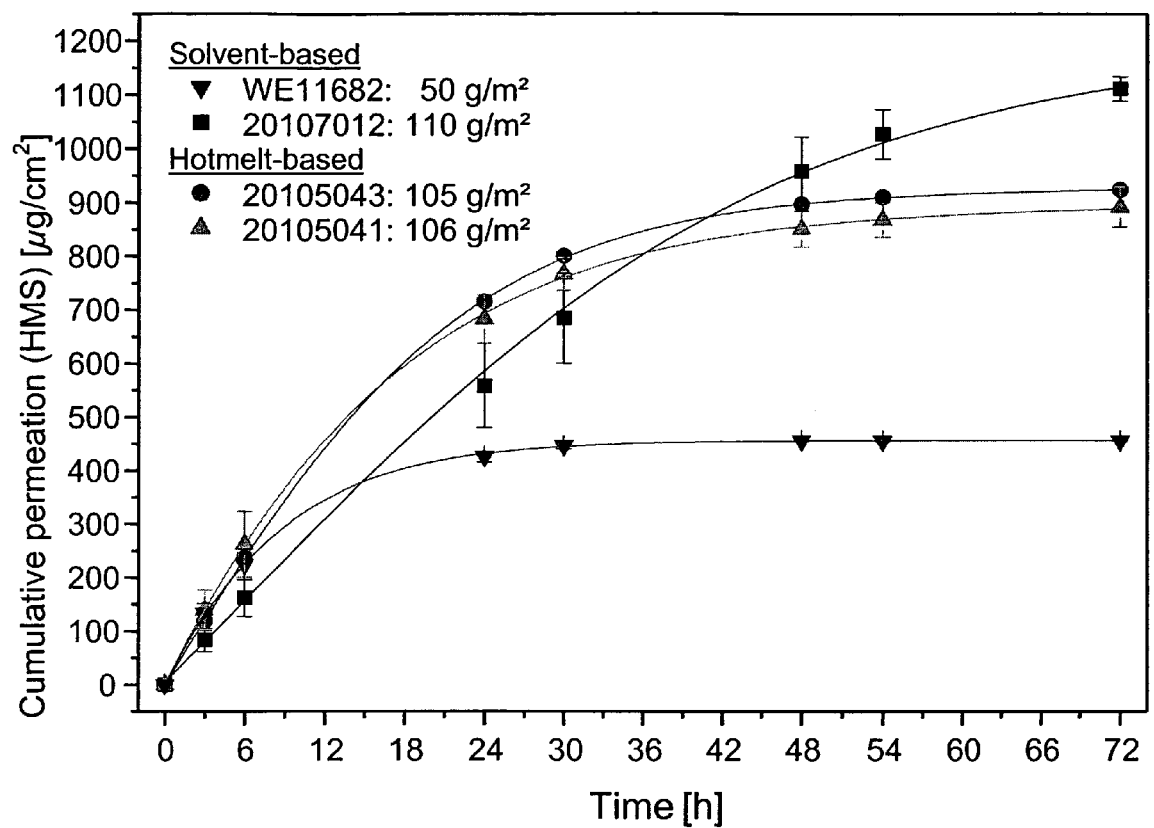
Figure 1a: Release through murine skin (HMS) from TTS containing 9% (w/w) Rotigotine

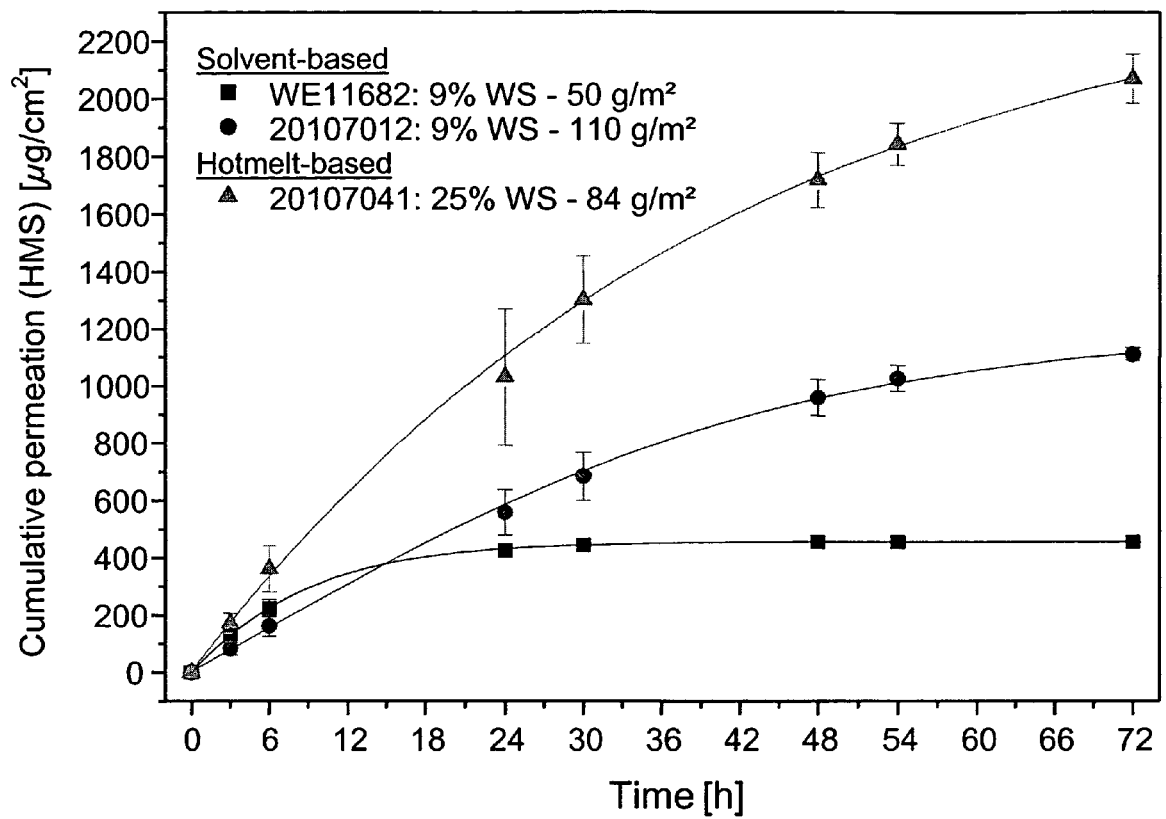
Figure 1b: WS permeation from hotmelt silicone TTS containing 25% Rotigotine (WS)

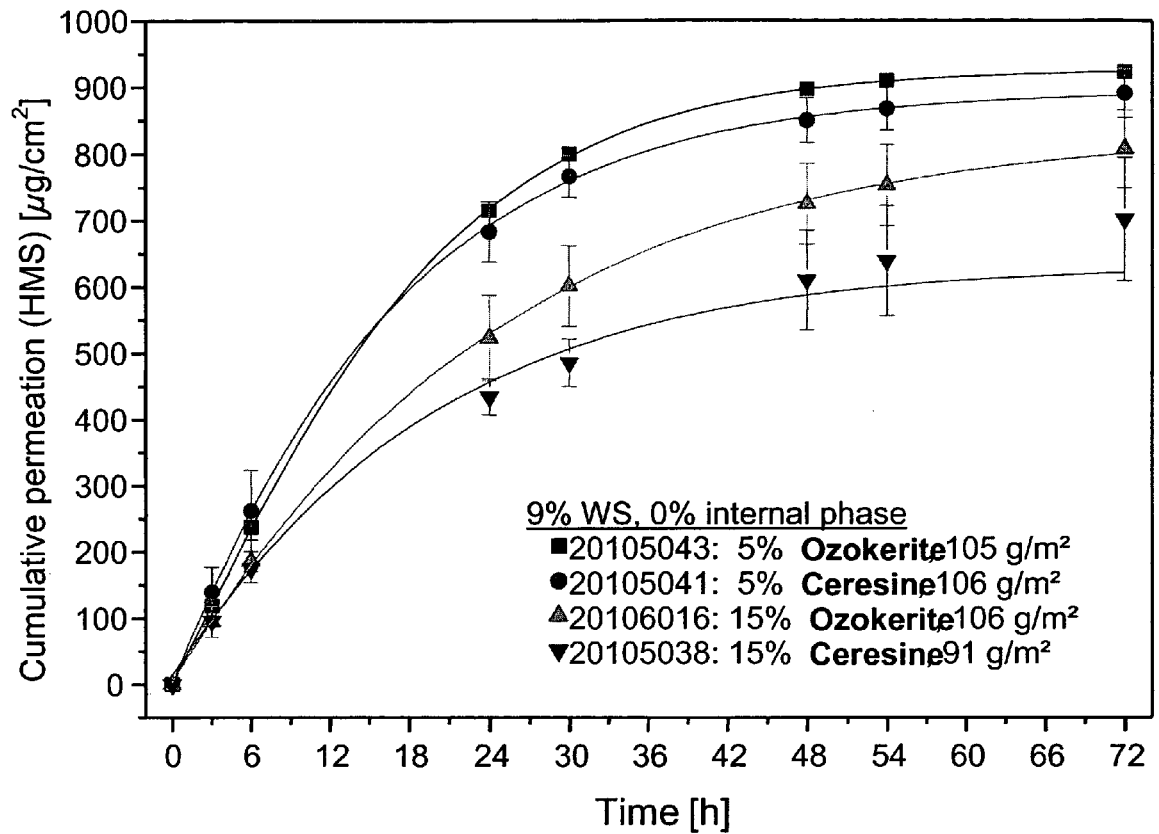
Figure 2: Effect of the wax content on Rotigotine (WS) permeation

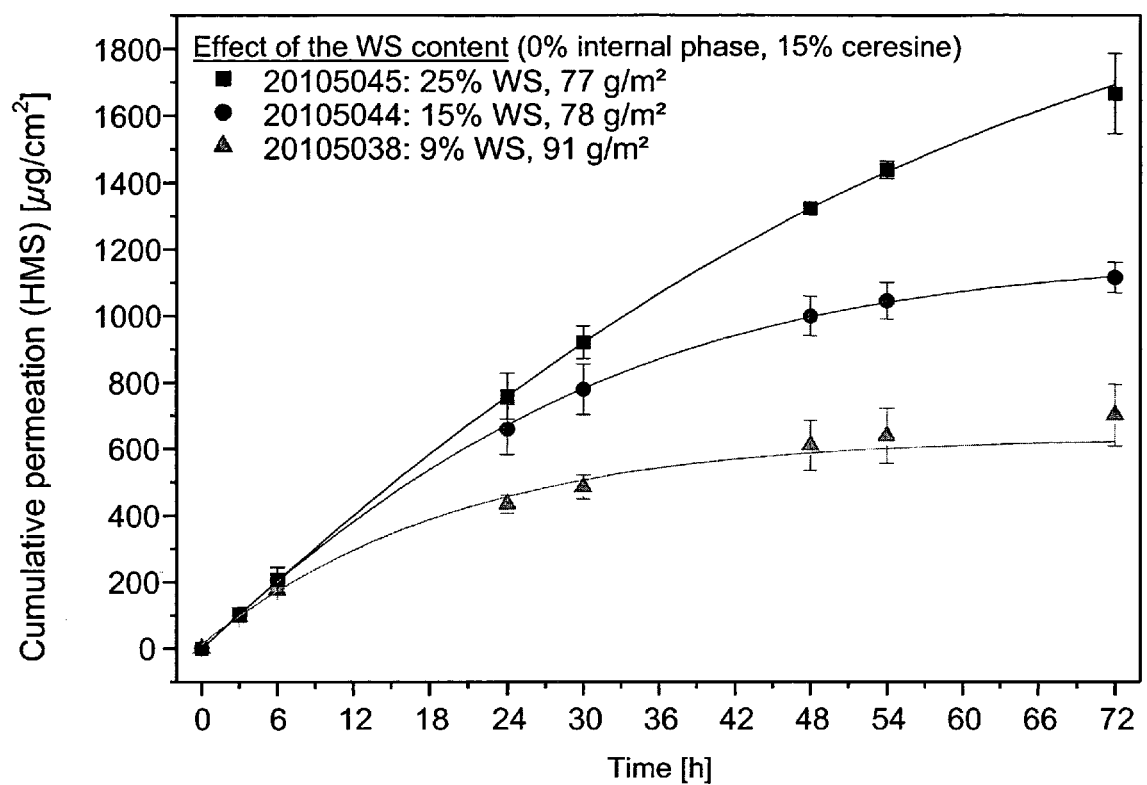
Figure 3a: Effect of the load level on Rotigotine permeation

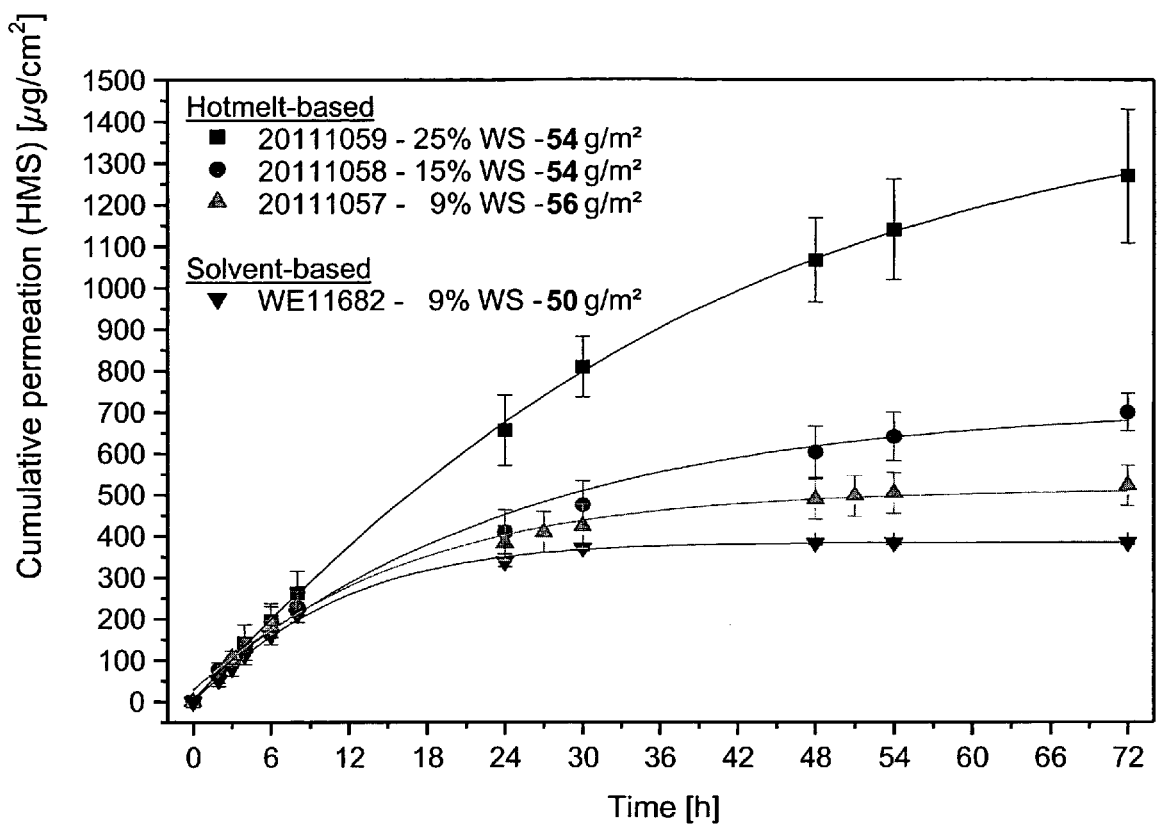
Figure 3b: Effect of the Rotigotine load level on Rotigotine permeation

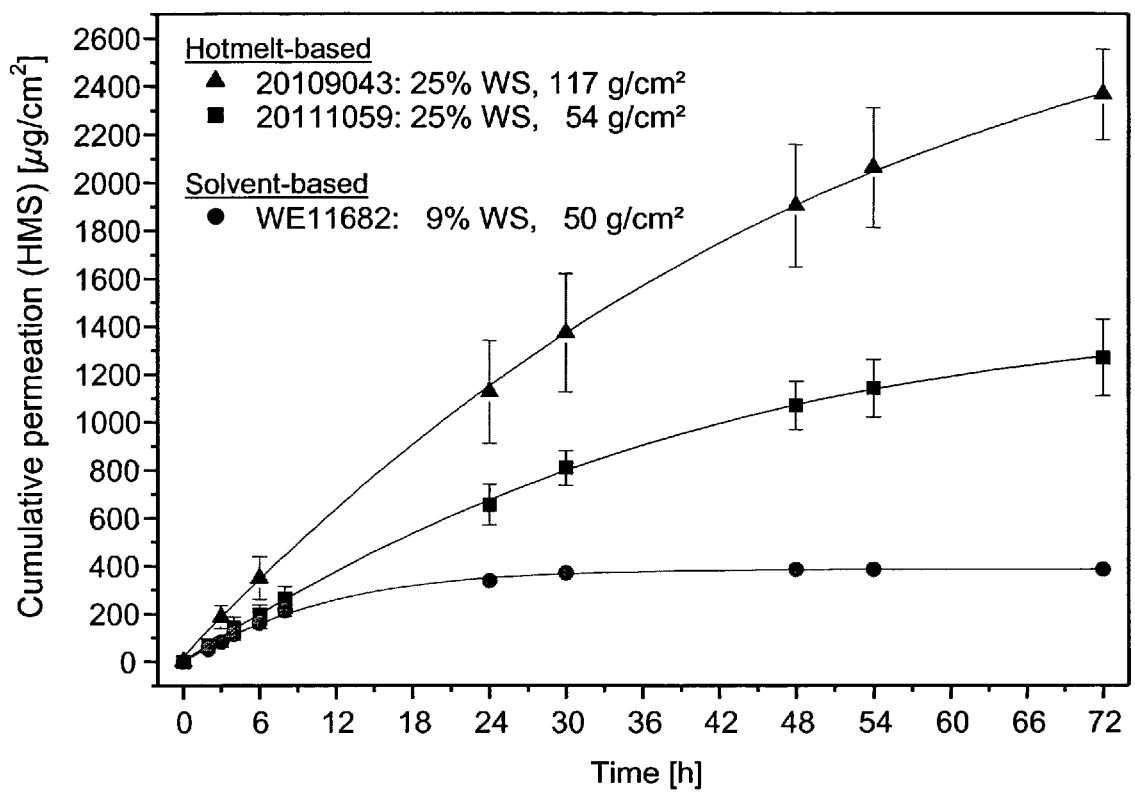
Figure 4: Effect of the matrix weight on Rotigotine permeation

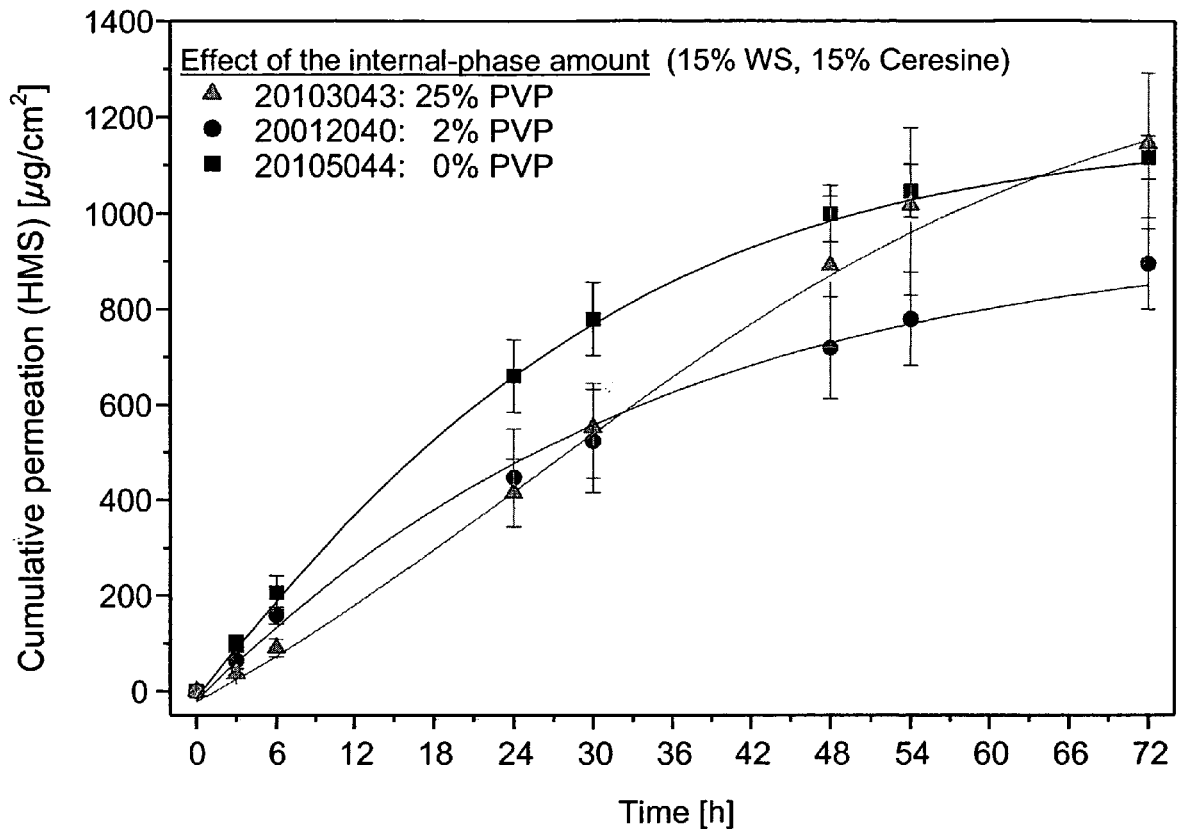
Figure 5a: Effect of the internal-phase (PVP) content on Rotigotine permeation

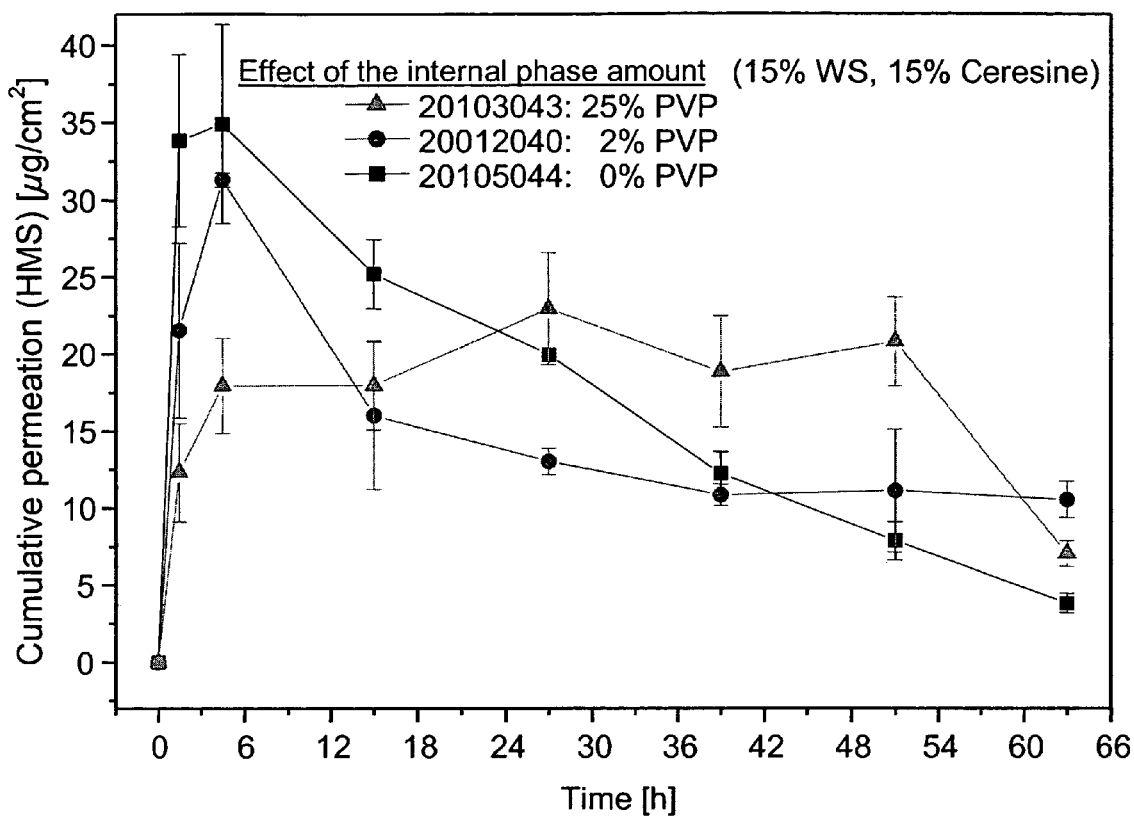
Figure 5b: Effect of the internal-phase (PVP) content on Rotigotine permeation

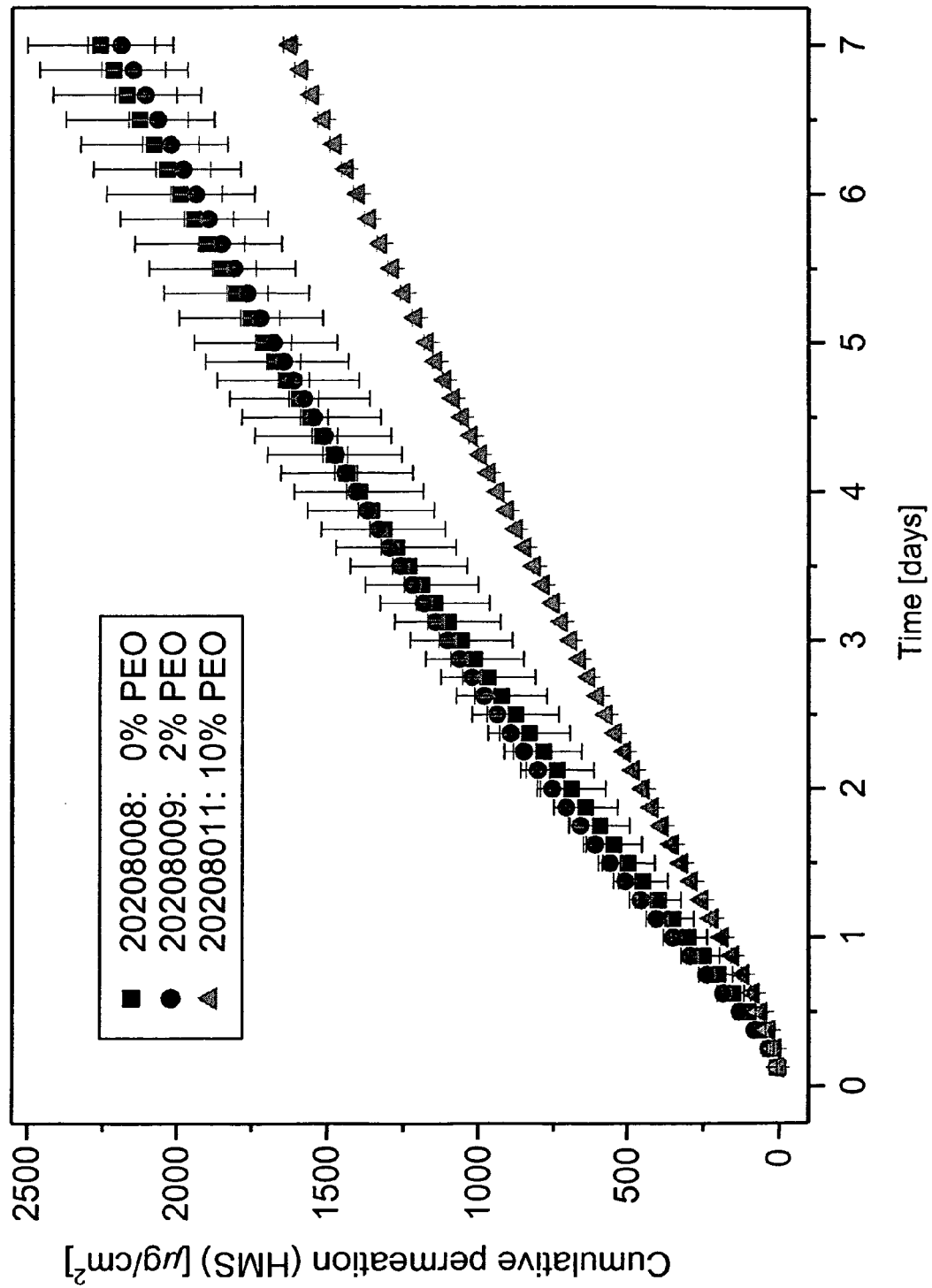
Figure 5c: Effect of the internal-phase (PEO) content on Rotigotine permeation

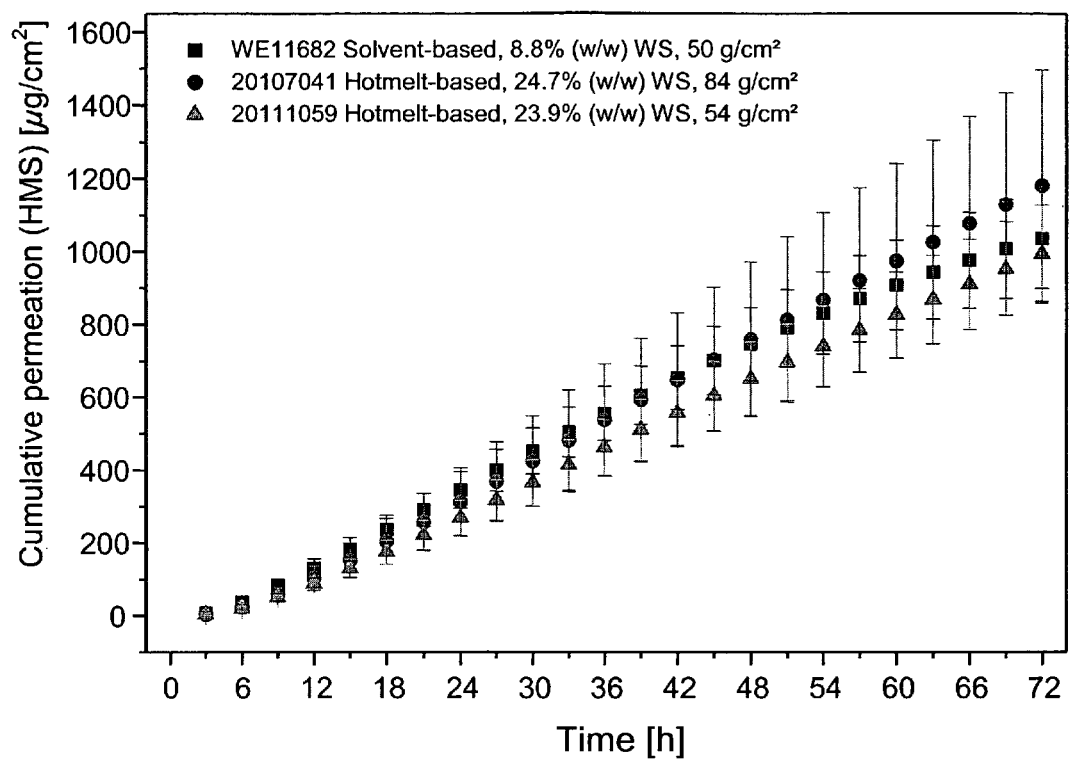
Figure 6a: Comparison of the cumulative Rotigotine permeation through human skin (EHS/SS)

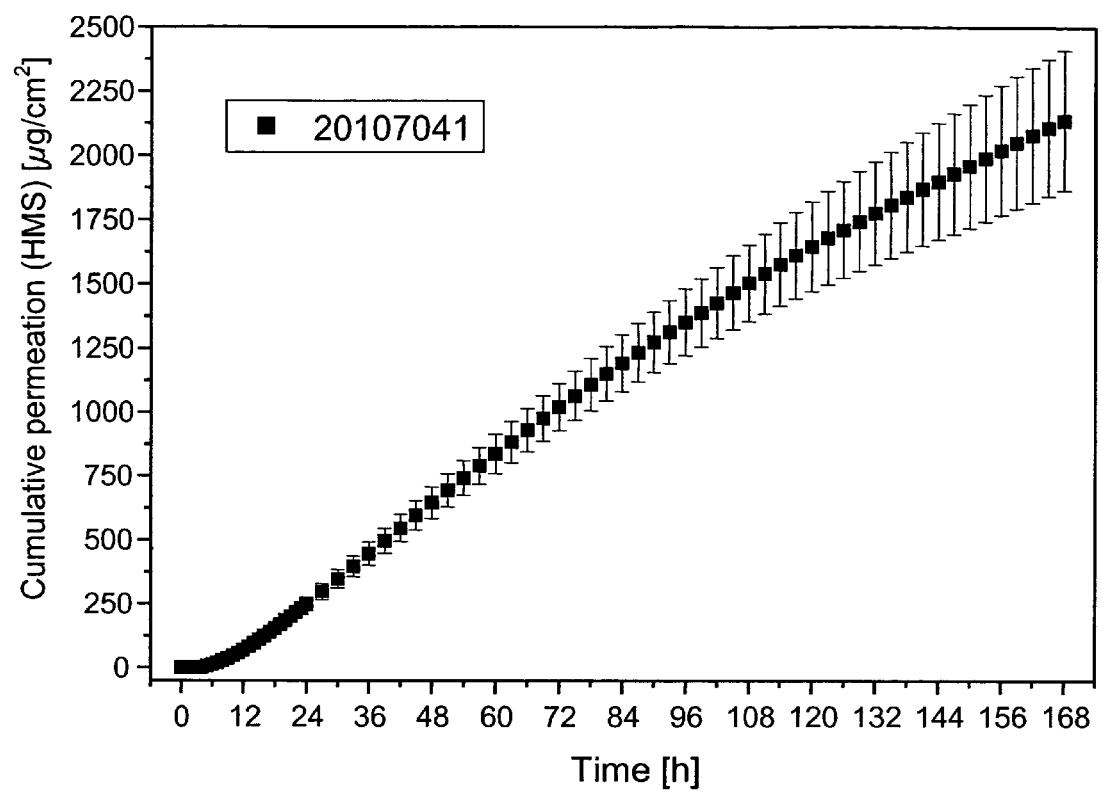
Figure 6b: Permeation of Rotigotine from a silicone-based hotmelt patch (25 weight% Rotigotine) through human skin

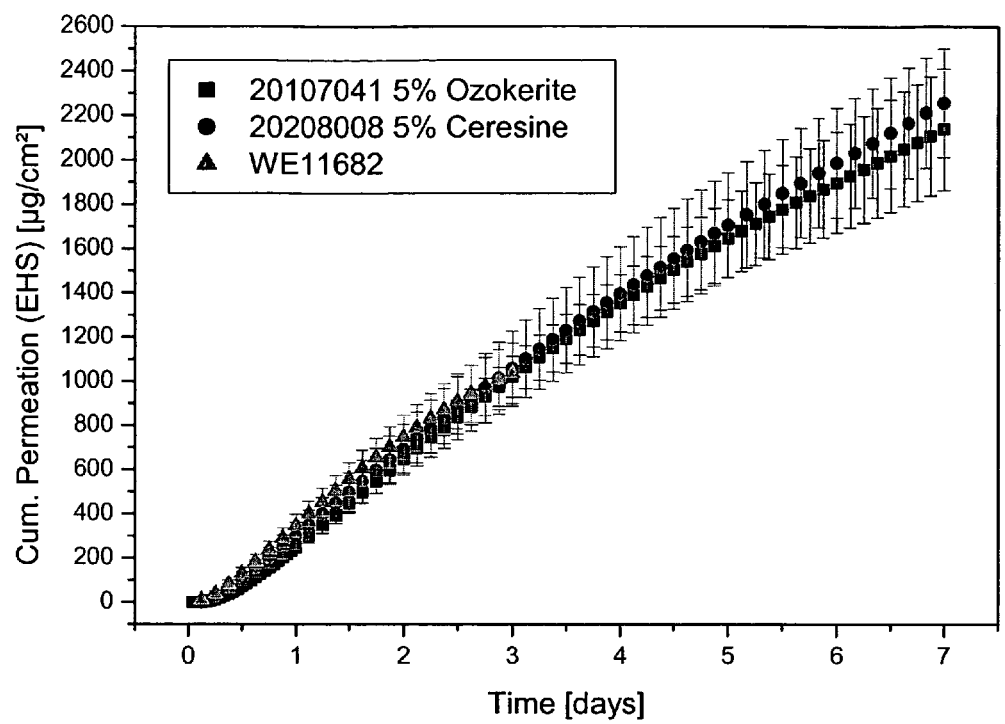
Figure 6c: Equivalence of the two hotmelt waxes (25% (w/w) Rotigotine) in terms of flux through human skin in comparison with the Phase III clinical sample

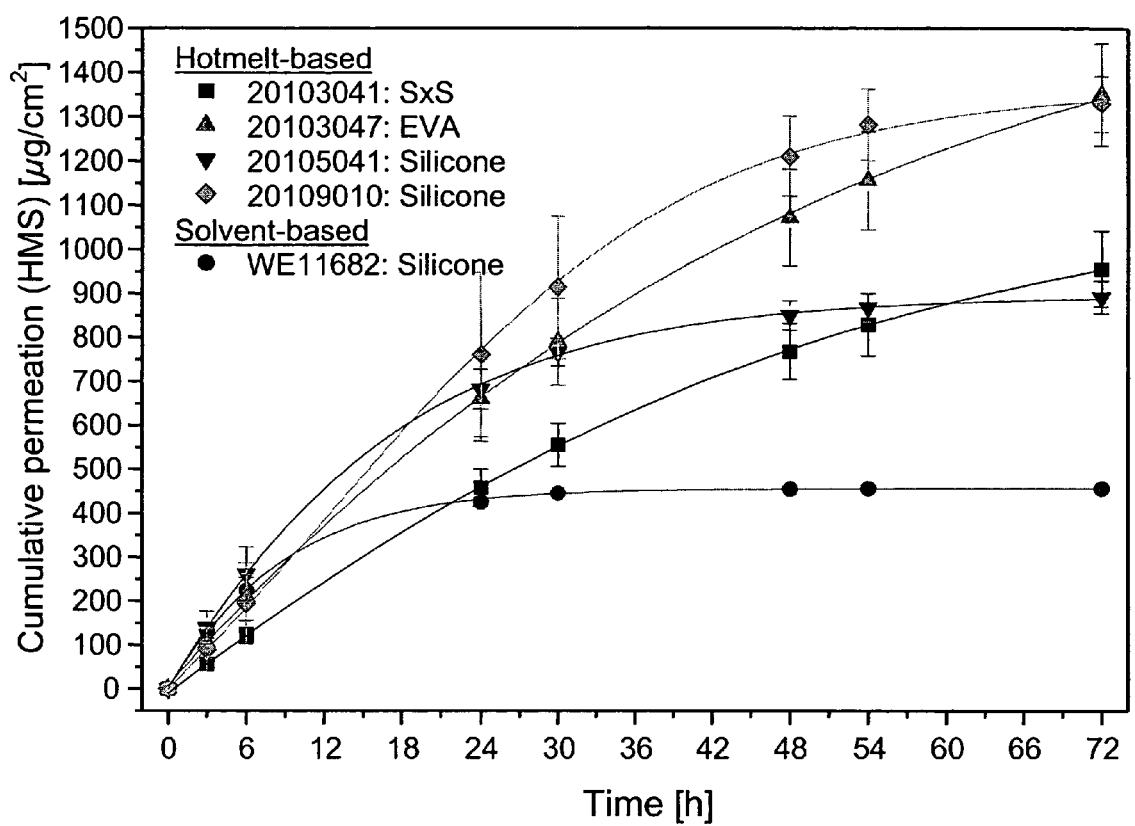
Figure 7: Rotigotine permeation from TTSs based on different hotmelt adhesives

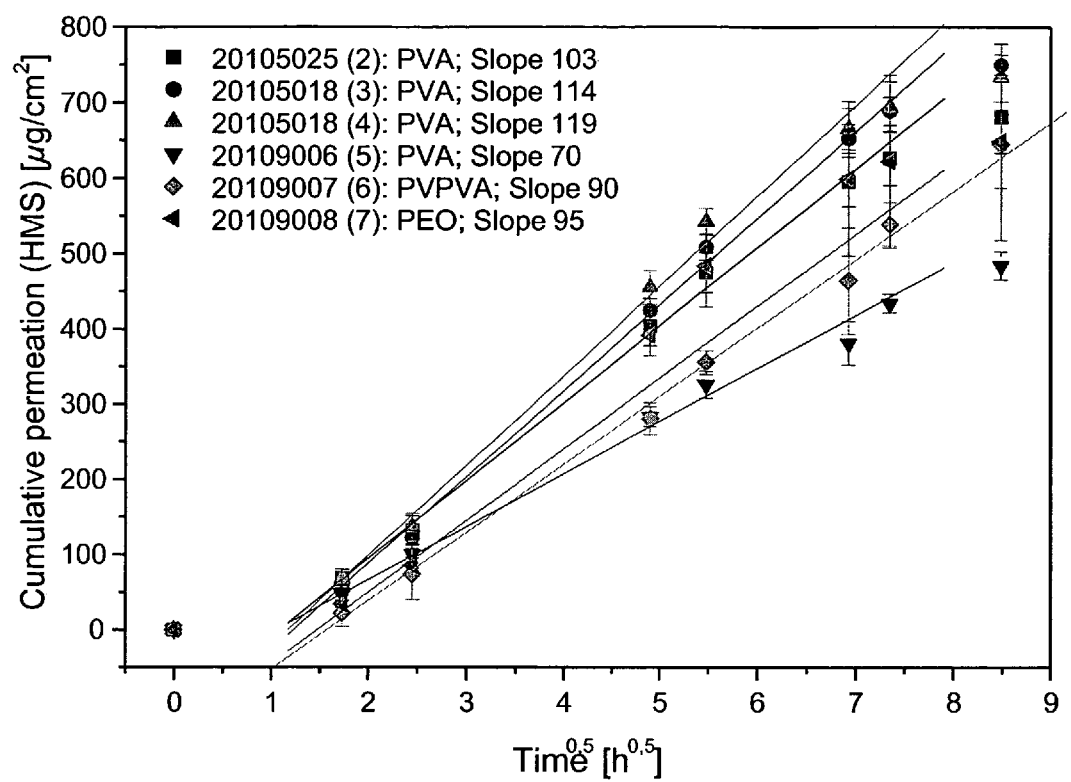
Figure 8: Rotigotine permeation from hotmelt silicone TTSs with different internal phases

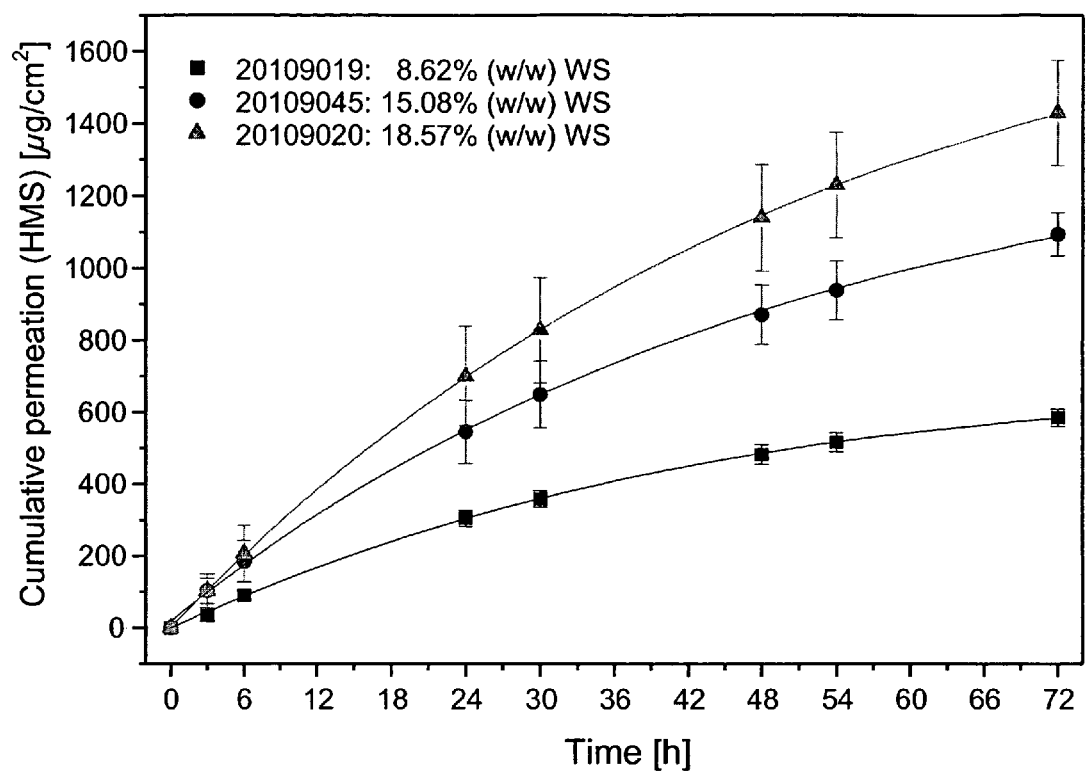
Figure 9: Rotigotine permeation from hotmelt EVA TTSs through murine skin Figure 9a: More highly loaded EVA hotmelt (20103047; 16.2% (w/w)) through human skin in comparison with the Phase III clinical sample (WE 11682; 9 % (w/w))
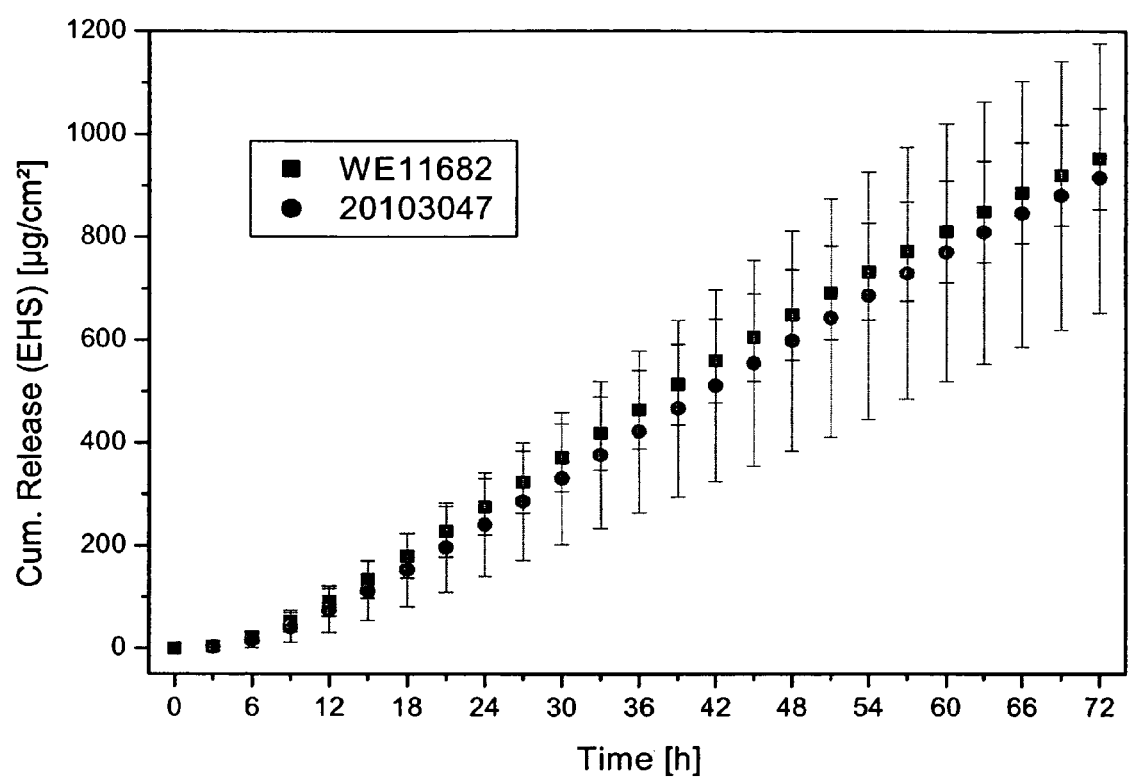

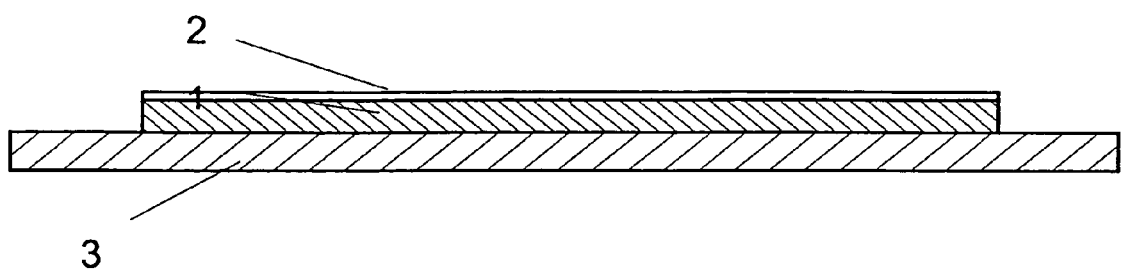
Figure 10: Schematic example of a TTS configuration

HOT MELT TTS FOR ADMINISTERING ROTIGOTINE

This invention relates to a transdermal therapeutic system (TTS) encompassing a Rotigotine-containing adhesive matrix, characterized in that the adhesive matrix contains a hot-meltable adhesive in which the active substance Rotigotine ((−)-5,6,7,8-tetrahydro-6-[propyl[2-(2-thienyl)ethyl)amino]-1-napthol) is dispersed and partly or completely dissolved.

The invention further relates to a method for producing a TTS that encompasses a adhesive matrix containing Rotigotine as the active substance, characterized in that, prior to the coating and laminating, the components of the adhesive matrix are melted and homogenized, without any solvent, at temperatures between 70 and 200° C. and preferably between 120 and 160° C.

Finally, this patent application relates to the use of Rotigotine for producing the adhesive matrix of a TTS by the hot-melting process.

Prior art has described various TTSs for the administration of Rotigotine.

WO 94-07468 discloses a system that contains as the active substance a salt in a diphasic matrix. That diphasic matrix consists of a hydrophobic polymer in which a silicate is dispersed to accept the hydrophilic medicinal salt, assisted by the additional use of organic solvents. The matrix is produced by drying the dispersion at 70° C. The Rotigotine content in the matrix is 2-5% by weight.

That system, however, has a number of drawbacks:
(1) Its production is a multi-stage, complex process. The active substance must be dissolved in water or in an aqueous solvent mixture, then mixed with the silicate, then mixed with an emulsifier so as to finally emulsify the aqueous solution with the polymer such as a silicone adhesive dissolved in an organic solvent, typically heptane, ethyl acetate or toluene. The resulting emulsion is difficult to manipulate.
(2) Organic solvents are used which, during the TTS production, have to be completely removed again so as to ensure an adequate shelf life as well as reproducible release characteristics of the TTS while preventing skin irritations. That increases the production cost. Up to the point where the adhesive contains the active substance, it is a discontinuous process.
(3) Handling organic solvents requires stepped-up safety precautions to prevent any environmental impact or exposure of the personnel involved in the TTS production. Solvent recovery/ separation equipment, measures for personnel protection and the disposal of solvents are all costly.
(4) On the one hand, the admixture of the active substance is limited by the degree of solubility of the Rotigotine in the solvent concerned. On the other hand, as the solvent is removed during the production process, the relative concentration of the active substance increases, which can lead to an oversaturation of the matrix with the active substance and to undesirable crystallization. This again places a limit on the maximum amount of the active substance that can be worked into the matrix. Yet a low-level charge of the active substance limits the release capacity of the matrix per unit of time and/or its functional lifespan due to a premature depletion of the active substance.
(5) The thickness of the matrix that can be obtained in one production step is limited to about 100 µm (equaling about 100 g/m$^2$) if it is to ensure the complete removal, in the drying process, of the solvent needed for its production. If adhesive matrices with a thickness greater than about 100 µm are required, they must be built up layer by layer, which is a complex and cost-increasing operation.
(6) The silicate or silicon oxide remaining in the adhesive patch constitutes a diffusion barrier for the active substance and may negatively affect the release of the latter. It also affects the water absorption of the adhesive patch. The formation of pores by the removal of water-soluble matrix components at the interface with the skin can lead to an insufficiently controllable release of the active substance.

WO 99/49852 describes a TTS with Rotigotine in its free-base form containing an acrylate- or silicone-based adhesive system. For producing either system, solvents are again used that will later have to be removed again, involving the same drawbacks and limitations described under (2) to (5) above.

In terms of the charge and release of Rotigotine, the two matrices described in WO 99/49852 have these additional shortcomings:

Silicone matrices: Assuming an emulsion or solution containing an active substance, the matrix can accept Rotigotine at about 15% by weight. In other words, there are limits to the admixability of active substances in silicone matrices. Increasing the Rotigotine admixture for instance in the production of multi-day patches is possible only by adding more matrix layers, which, however, requires several procedural steps that make the production more complex and expensive.

Acrylate matrices: By means of solvent coating, acrylate matrices can accept Rotigotine at up to about 40% by weight. However, the higher absorption capacity of these matrices for Rotigotine is offset by a reduced capacity to release it onto the skin due to an agent-distribution coefficient that is inferior to that of silicone systems. Obtaining adequate Rotigotine plasma levels from these systems requires very high charge rates. Yet relatively large amounts of the active substance remain in the patch after its use, increasing the effective cost of these systems while being undesirable from the perspective of drug safety.

It is therefore the objective of this invention to provide a TTS that avoids the drawbacks and limitations associated with the use of solvents. In particular, the Rotigotine TTS should offer the highest possible degree of flexibility in admixing Rotigotine even in larger amounts while releasing the Rotigotine in therapeutically effective quantities.

The problems described above have been solved by providing, as the first of its kind, a TTS with a Rotigotine-containing adhesive matrix, characterized in that the adhesive matrix is produced in a hot-melting process, whereby the adhesive matrix contains a hot-meltable adhesive in which Rotigotine as the active substance ((−)-5,6,7,8-tetrahydro-6-[propyl[2-(2-thienyl)ethyl)amino]-1-napthol) is dispersed and partly or completely dissolved.

ILLUSTRATIONS

FIGS. 1 *a* and *b* show comparisons of Rotigotine permeation through murine skin (HMS), between a hot-melt silicone TTS and a solvent-based silicone TTS. FIG. 1*a* illustrates the release from either TTS each with a Rotigotine content of 9% by weight. FIG. 1*b* shows the effect of a higher Rotigotine charge on the Rotigotine permeation from the hot-melt TTS through the murine skin.

FIG. 2 shows the effect of the wax content on the permeation through murine skin of Rotigotine from the hot-melt silicone TTS with a constant 9 weight-% charge of the active substance.

FIGS. 3 *a* and *b* show the effect of the Rotigotine charge on the Rotigotine permeation through murine skin from the silicone-based hot-melt TTS in the presence of 15% wax (3a) and, respectively, 5% wax (3b).

FIG. 4 illustrates the effect of the matrix weight on the Rotigotine permeation through murine skin from a silicone-based hot-melt TTS.

FIGS. 5 a and b show the effect of the content of the internal-phase component (PVP) on the cumulative (5a) and linear (5b) permeation of Rotigotine from the hot-melt TTS through murine skin. FIG. 5c shows the effect of the PEO concentration on the cumulative Rotigotine permeation through human skin from a silicone-based hot-melt TTS FIG. 6a shows the cumulative 72-hour permeation of Rotigotine from a hot-melt silicone TTS through human skin in comparison with that from a solvent-based silicone TTS. FIG. 6b shows the cumulative 7-day permeation of Rotigotine from a hot-melt silicone TTS through human skin.

FIG. 6c shows the cumulative 7-day Rotigotine permeation through human skin from a hot-melt silicone TTS containing 5% ozokerite or 5% ceresine.

FIG. 7 shows the cumulative Rotigotine permeation, from hot-melt TTS with different hot-meltable adhesives, through murine skin.

FIG. 8 shows the cumulative permeation, through murine skin, of Rotigotine from silicone-based hot-melt TTS produced in an extruder with different internal-phase components and a Rotigotine content of 9%.

FIG. 9 shows the cumulative permeation, through murine skin, of Rotigotine from EVA-based hot-melt TTS produced in the extruder with different Rotigotine concentrations. FIG. 9a shows the cumulative permeation, through human skin, of Rotigotine from an EVA-based hot-melt TTS in comparison with the solvent-based silicone TTS.

FIG. 10 illustrates an example of a TTS structure with an active substance-containing adhesive matrix (1), a backing (2) that is inert to the constituent components of the adhesive matrix, and a protective film (3) that must be removed before use.

DESCRIPTION OF THE INVENTION

Figure 11:
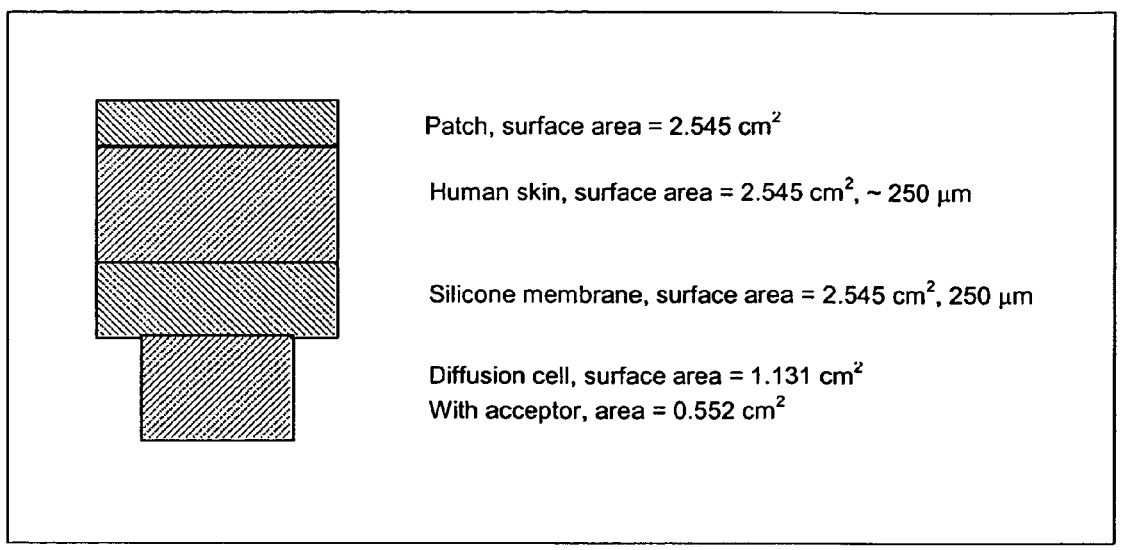

It was surprising to find that Rotigotine lends itself superbly to processing by the hot-melt method, that it remains stable under short-term heating to temperatures up to at least 160° C., that it can be homogeneously worked into matrices produced by the hot-melt process, and that it is released from the hot-melt matrices in continuous fashion and at a therapeutically desirable rate.

In particular, the inventors were surprised to find that the Rotigotine, being susceptible to oxidation, remains stable in the hot-melt process even when heated to temperatures around 160° C. While at higher temperatures in an oxygen-containing atmosphere, Rotigotine tends to decompose in oxidative fashion, it is amazingly stable in the hot adhesive melt and is present in the matrix at a purity level that is routinely better than 98% and generally over 99% (measured at 220 nm and 272 nm per HPLC; see tables 2, 3 and 4).

The preferred method is to introduce the Rotigotine in its solid form into the homogenized matrix melt, i.e. the Rotigotine is not melted until it is in the hot matrix. Following brief homogenization the Rotigotine-containing adhesive matrix is cooled again so that, in general, the Rotigotine is exposed to thermal stress for less than 5 minutes and preferably less than 4, 3 or even 1 minute(s). The Rotigotine will then be present in the solidified melt. During that process the Rotigotine is largely protected from critical environmental factors (light, oxygen).

The TTSs thus produced by the hot-melt method accept a high Rotigotine charge of up to over 40% by weight relative to the weight of the matrix.

Overall, the TTSs produced according to this invention by the hot-melt method offer a number of advantages over prior-art solvent-based TTSs:

Since the Rotigotine can be directly inserted in the adhesive melt, it eliminates the solvent-related problems when higher active-substance concentrations are used. Consequently, substantially higher Rotigotine concentrations (up to over 40 weight %) can be introduced in the TTS, in simple fashion, than would be possible in a solvent- and silicone-based process where Rotigotine concentrations of more than about 15 weight % can no longer be worked in as a solution. It is thus possible to introduce surprisingly large Rotigotine amounts even in relatively thin matrices, and in only one procedural step.

The thickness of the layer can be varied over a wide range. For example, matrices having a weight of more than 100 $g/m^2$ and even more than 200 $g/m^2$ can be produced in a single step without difficulty. It follows that, in combination with the higher Rotigotine concentration, a Rotigotine content in the TTS matrix of up to 8 $mg/cm^2$ or even more is attainable. In contrast to that, it is not possible in a single-step operation to introduce a Rotigotine charge of more than about 1.5 $mg/cm^2$ in a silicone TTS produced by the solvent-based process.

The use, removal, recovery or disposal by incineration of organic solvents and the associated need for safety precautions in TTS production are eliminated.

Hot-melt technology permits the continuous production of the TTS matrix from the weighing of its individual components all the way to lamination. That type of production cycle essentially offers the following advantages:

Processing times are substantially reduced.

The charge volume is determined via the operating time of the production facility. This avoids having to switch over to larger facilities with the associated scale-up problems and/or additional validation requirements.

GMP-compliant production is possible using compact equipment with a small footprint.

Using a suitable softener such as wax and/or the optional incorporation of an internal phase permits delayed release of the Rotigotine from the adhesive matrix. An appropriate TTS configuration makes it possible to produce TTSs that release Rotigotine over a span of several days, for instance 5, 6 or 7 days, in continuous fashion and therapeutically effective quantities.

Therefore, one object of this invention is a transdermal therapeutic system (TTS) that encompasses a Rotigotine-containing adhesive matrix, characterized in that the adhesive matrix contains a hot-meltable adhesive.

Another object of the invention is a transdermal therapeutic system (TTS) incorporating a Rotigotine-containing adhesive matrix, characterized in that the adhesive matrix contains a hot-meltable adhesive in which the active substance, Rotigotine ((−)-5,6,7,8-tetrahydro-6-[propyl[2-(2-thienyl)ethyl)amino]-1-napththol), is dispersed and partly or completely dissolved.

In another implementation of the invention, the hot-meltable adhesive matrix contains a Rotigotine prodrug instead of Rotigotine, i.e. a compound such as an ester that is broken down into Rotigotine or metabolized in the patient's body for instance through esterase in the blood or skin in therapeutically effective quantities. The prodrug should preferably release Rotigotine at a rate by which a therapeutically effective steady-state Rotigotine concentration is attained in the plasma. These concentrations are preferably in the 0.05 to 20 ng/ml range, better yet between 0.1 and 10 ng/ml and ideally between 0.2 and 5 ng of Rotigotine/ml plasma.

Another object of this invention is a TTS with a Rotigotine-containing adhesive matrix produced by the hot-melt method employing a process in which the Rotigotine is introduced, in molten or preferably in its solid form, into the 70-200° C. melt of the solvent-free adhesive matrix. The Rotigotine is introduced in a solvent-free melt that is preferably heated to 100-170° C., desirably to 120-160° C. and ideally to 130-150° C., and then processed and cooled within 5 minutes, preferably within 3 minutes and ideally within a maximum of 1 minute after the admixture of the Rotigotine.

The term "transdermal therapeutic system" refers to a pharmaceutical formulation or device that lends itself to the transdermal administration of an active substance through the skin of a mammal, especially through the human skin, in therapeutically effective quantities.

The term "hot-melt process" refers to a method that employs thermal energy for melting the hot-meltable adhesive and the optionally provided internal phase, thus obviating the need for solvents in the production of the adhesive matrix. By "hot-melt process" this patent application also subsumes a procedural variation involving work at temperatures below the melting point of Rotigotine, whereby the adhesive melt contains the Rotigotine in its solid form.

The term "solvent-free" as used in this patent application indicates that in producing the adhesive matrix no solvents are used that would have to be removed again in the course of the production process.

The term "hot-meltable adhesive" refers to an adhesive which, when applied to the skin, is pressure-sensitive and which can be processed by the hot-melt method at process temperatures of 70° C. to 200° C., preferably 100° C. to 170° C., desirably 120° C. to 160° C. and ideally at temperatures between 130° C. and 150° C. The "hot-meltable adhesive" may consist of an adhesive or a mixture of different adhesives that are individually hot-meltable. Alternatively, the "hot-meltable adhesive" may be a mixture composed of an adhesive and a suitable softener.

These hot-meltable adhesives preferably have a dynamic viscosity which at 160° C. and especially at temperatures between 130° C. and 150° C. is at the most 150 Pa·s, preferably not more than 120 Pa·s, desirably less than 100 Pa·s and ideally less than 80 or even 60 Pa·s.

Examples of adhesives that are not hot-meltable per se include the commercially available silicone adhesives. At the aforementioned processing temperatures, silicone adhesives would be too viscous, having a dynamic viscosity of more than 150 Pa·s.

Existing patent literature discusses a variety of methods for making highly viscous silicone adhesives hot-meltable by admixing suitable additives (softeners). Examples of such softeners for silicones include glycerol monolaurate or lauryl acetate as described in EP 835 136, waxes along the formula R—C(O)—OR' as described in EP 360 467, alkylmethyl siloxane waxes as described in EP 524 775, siloxated polyether waxes as described in EP 663 431, or organic waxes as described in U.S. Pat. No. RE 36,754.

The softeners are usually added to the silicone adhesive in quantities from 1-30 weight % relative to the overall hot-meltable adhesive mixture. The preferred softeners are organic waxes as described in U.S. RE 36 754, such as ozokerite, ceresine, paraffin, candelilla, carnauba, bee's wax or mixtures of these waxes, with ozokerite and ceresine being particularly preferred.

Ready-mixed hot-meltable silicone adhesives, especially mixtures of silicone adhesives and ceresine or ozokerite, are available from Dow Corning in Michigan. Adding for instance 10 weight % of ceresine to a silicone adhesive succeeded in reducing the dynamic viscosity of the resulting adhesive mixture, at a processing temperature of 160° C., from over 150 Pa·s to below 50 Pa·s. That type of silicone-based adhesive mixture lends itself well to being processed by the hot-melt method within a temperature range from 100° C. to 200° C. and especially in the range between 120° C. and 160° C.

A surprising discovery showed that hot-meltable silicone adhesives are superbly suitable for the transdermal administration of Rotigotine.

Therefore, one object of this invention is a transdermal therapeutic system (TTS) that encompasses a Rotigotine-containing adhesive matrix, characterized in that the adhesive matrix contains a hot-meltable adhesive in which the active substance, Rotigotine((−)-5,6,7,8-tetrahydro-6-[propyl[2-(2-thienyl)ethyl)amino]-1-napththol), is dispersed and partly or completely dissolved, said hot-meltable adhesive containing a suitable mixture of a silicone-based adhesive and at least one softener.

Another aspect of this invention consists of a TTS that encompasses a adhesive matrix containing:
(a) 50-99 weight % of an adhesive mixture composed of
  (i) 70-99 weight % of an amine-resistant silicone adhesive
  (ii) 1-30 weight % of a suitable softener
(b) 1-40 weight % Rotigotine or a Rotigotine prodrug.

In a preferred implementation of the invention, the said silicone-based hot-meltable adhesive consists of
(a) 70-99 weight % of an amine-resistant silicone adhesive and
(b) 1-30 weight %, preferably 3-15 weight % and most desirably 4-10 weight % of an organic wax preferably selected from the group encompassing ozokerite, ceresine, paraffin, candelilla, carnauba, bee's wax or mixtures of these waxes, with particular preference given to ozokerite and especially ceresine.

As shown in FIG. 1a, a silicone-based hot-melt TTS of this simple composition produces in-vitro Rotigotine permeation rates comparable to those of prior-art, therapeutically effective, solvent-based silicone TTSs.

FIG. 1b shows that, with an appropriately high loading of the hot-melt silicone TTS per this invention, in-vitro flux rates can be achieved that are clearly above the rates attainable with prior-art, clinically effective, solvent-based silicone patches.

For the purpose of this patent application the term "hot-melt TTS" refers to a TTS whose adhesive matrix was produced by the hot-melt method, meaning by the solvent-free melting of the hot-meltable adhesive and, where applicable, additional components.

A surprising discovery showed that adding wax, especially organic wax such as ceresine or ozokerite, also has an effect on the in-vitro murine-skin permeation of Rotigotine from the hot-melt silicone TTS. As is evident from FIG. 2, Rotigotine's permeation rate decreases as the wax concentration increases. This can be explained by a partial Rotigotine distribution in the wax and a concomitant retardation effect.

This property of the wax is significant especially for developing a TTS designed for application over several days, for instance 7 days. That type of multi-day patch requires a high loading of Rotigotine, which poses the risk of an excessive release of Rotigotine at the beginning of the application phase ("dose dumping"). It is therefore desirable to work into the TTS a component that controls the release of the active substance. This could be in the form of a membrane attached to the bottom of the matrix for controlling the release of the active substance. However, such a membrane increases material cost and makes the TTS structure more complex. It would therefore be desirable, instead of adding such a membrane, to include suitable retardant components in the matrix.

Due to the surprising discovery that the wax content in the matrix serves to retard the release of the active substance, varying the wax content will not only modify the dynamic viscosity of the adhesive but additionally offers the surprising additional option of regulating the active-substance release.

As the wax content increases, the dynamic viscosity of the silicone adhesive initially drops off sharply to where the wax content is about 5 weight %, after which it decreases only slightly. Thus, when the wax content is 4-10 weight %, the dynamic viscosity of the silicone adhesive is at a level that suitably permits hot-melt processing while at the same time its effect on the Rotigotine release is minor. Higher wax concentrations will additionally produce a retardation effect.

FIGS. 6a and 6c show that adding 5 weight-% of an organic wax to a TTS charged with relatively large quantities of Rotigotine (in this case about 25 weight-%) will generate flux rates through human skin that are comparable to those obtained with a less highly charged (9 weight-%) solvent-based TTS. Consequently, TTSs can be produced for an extended active-substance release, for instance over 7 days (FIGS. 6b and 6c).

Similarly, the effect of the wax on the rheological properties of the TTS is surprising. If an organic wax is used as the softener for a silicone adhesive, the dynamic viscosity of the adhesive mixture decreases at elevated temperatures, which in excellent fashion permits the processing of the silicone-based adhesive mixture by the hot-melt method. At the same time, the Theological properties of the silicone, such as its cohesivity, unexpectedly remain fairly unaffected at room temperature, so that the typical problems with hot-meltable adhesives such as cold flux on the patient's skin are not encountered.

Suitable silicones include all of the silicone adhesives employed in adhesive-patch technology. The preferred silicone adhesives are amine-resistant, pressure-sensitive polyorganosiloxane adhesives. In most cases, the silicone adhesives are polydimethyl siloxanes, but in principle it is just as possible to use in place of the methyl groups other organic radicals such as ethyl or phenyl groups. Amine-resistant silicone adhesives generally offer the advantage that they contain no or only few free silanol functions since their Si—OH groups were alkylated. That type of adhesives has been described in EP 180 377. The particularly preferred adhesives include condensates or mixtures of silicone resins and polyorganosiloxanes as described for instance in U.S. RE 35 474.

These silicone adhesives are commercially available and are marketed for instance by Dow Corning as Bio-PSA Q7-4300 or Bio-PSA Q7-4200. Also available from Dow Corning are hot-meltable silicone adhesives that are mixtures of PSA 7-4300 with organic waxes such as ozokerite or ceresine.

The active substance, Rotigotine, may be present at concentrations of 1 to more than 40 weight % relative to the weight of the total adhesive layer, either as a salt or in free-base form. Preferably, the adhesive matrix contains the Rotigotine in free-base form. Alternatively, the Rotigotine may be in the form of a prodrug, for instance a Rotigotine ester or Rotigotine carbamate.

Unlike the solvent-based silicone adhesives whose active-substance content is 15 weight % at the most, the adhesive matrices of hot-melt TTSs can accept significantly greater amounts of Rotigotine without requiring any additional technical measures. That again provides greater flexibility in selecting the permeation rate and the release period of the hot-melt TTS.

As is evident from the example of a silicone-based hot-melt TTS in FIGS. 3a and 3b, a higher Rotigotine charge allows for a higher flux rate through mammalian skin as well as a longer Rotigotine release time. In applying a TTS on human skin, the particular effect of a higher Rotigotine concentration is an extended Rotigotine release while from an 8-9% Rotigotine concentration on up the permeation rate through human skin increases only marginally.

The preferred Rotigotine or Rotigotine-prodrug concentrations in the adhesive layer are 4-40 weight %, especially 9-30 weight % and more specifically 9-25 weight % or 15-25 weight %, for 7-day patches they are 20-40 weight % and especially 25-35 weight %, relative to the total weight of the adhesive layer.

Tests on a bovine udder model served to determine whether a silicone-based hot-melt TTS with a high Rotigotine charge (>15 weight-%) can be tolerated by the skin. To that effect, the vital capacity of the cells as well as the $PGE_2$ synthesis were measured following application of a corresponding Rotigotine hot-melt TTS (5% ceresine, 2% PEO, 25-30% Rotigotine).

Applying the TTS per this invention did not cause the cell activity to differ significantly from that of an untreated skin, whereas in terms of the $PGE_2$ synthesis there was a slight initial increase which, however, was no longer detectable 5 hours after the application. By comparison, treatment of the skin with a 10% SDS-solution resulted in a significant cell lethality rate (over 50% after 5 hours) and a substantially elevated $PGE_2$ synthesis (>60% after 5 hours), indicating an inflammatory reaction. This suggests that, a high Rotigotine charge notwithstanding, the hot-melt TTSs per this invention, lending themselves well to a Rotigotine application over several days, do not cause any significant irritation of the skin.

Varying the layer thickness of the adhesive matrix serves as an additional element in controlling the Rotigotine release rate and duration. The example of a hot-melt silicone TTS in FIG. 4 shows the effect of the weight of the matrix on the in-vitro permeation of Rotigotine through murine skin.

The thickness of the adhesive matrix can be flexibly selected over a wide range and in one single procedural step, since the layer thickness is not subject to the limitations associated with the solvent-based method. The layer thickness may be between 30 and 300 μm, preferably between 50 and 150 μm and most desirably between 50 and 120 μm.

The weight of the adhesive matrix of the TTS according to this invention is preferably between 30 and 300 $g/m^2$, desirably between 50 and 150 $g/m^2$ and ideally between 50 and 120 $g/m^2$; for 7-day patches it is preferably 70-200 $g/m^2$, desirably 80-180 $g/m^2$ and ideally 100-160 $g/m^2$.

The preferred Rotigotine content in the matrix is between 0.4 $mg/cm^2$ and 8 $mg/cm^2$, depending on for how long the TTS is to be applied.

For a 1-day TTS the preferred concentration is between 0.4 and 1.5 $mg/cm^2$ and most desirably between 0.4 and 0.8 $mg/cm^2$.

The average therapeutically required dose for adults is about 6 mg of Rotigotine per day. Hence, a 7-day patch requires an average of about 42 mg of the active substance per TTS. For safety considerations, clinically employed transdermal systems are assumed to draw only about 50-60% of the TTS supply, which is why a 7-day TTS should contain at least 70 to 84 mg of the active substance.

Consequently, given a 7-day-patch TTS size of preferably 10-30 cm² and most desirably 15-25 cm², the preferred Rotigotine charge will be as follows:

| Patch Size in cm² | Minimum Rotigotine Content in mg/cm² |
|---|---|
| 10 | 7.0-8.4 |
| 15 | 4.7-5.6 |
| 20 | 3.5-4.2 |
| 25 | 2.8-3.4 |
| 30 | 2.3-2.8 |

Accordingly, the preferred Rotigotine or Rotigotine prodrug content in 7-day patches is between about 2 mg/cm² and 8 mg/cm², desirably between about 2.8 mg/cm² and 5.6 mg/cm² and ideally between 3.1 and 5.6 mg/cm².

So far, prior art has not disclosed any TTS for the administration of Rotigotine in therapeutically significant quantities at this high level, which at this point is possible only by the variable charging and layer thickness of the hot-melt TTS. The high Rotigotine concentration of up to over 40 weight % makes it possible even for a 7-day TTS containing an appropriately large amount of Rotigotine to produce relatively thin matrices with a layer thickness of 80-200 μm, preferably 80-180 μm and ideally 80-160 μm.

Another object of this invention therefore includes TTSs for the administration of Rotigotine in therapeutically effective quantities, characterized in that they feature a Rotigotine concentration in the adhesive matrix of at least 2.0 mg/cm², preferably at least 2.8 mg/cm² and most desirably at least 3.1 mg/cm² or at least 3.4 mg/cm². Preferred are TTSs containing matrices with a Rotigotine charge rate of over 20 weight % and a matrix weight of under 200 g/m², for instance a weight of between 80 and 180 g/m² and most desirably between 80 and 160 g/m² (which corresponds to a layer thickness of about 80-200 μm).

As an option, the adhesive layer (also referred to as the adhesive matrix) may contain, in addition to the Rotigotine and the adhesive mixture, a component that serves as the internal phase.

In particular, the internal-phase component serves as a solubilizer and crystallization inhibitor while contributing to a uniform distribution of the active substance in the adhesive matrix. The internal-phase component also helps augment moisture absorption of the patch on the skin.

For use in the hot-melt process, the most suitable internal-phase components are those exhibiting at temperatures below 170° C. a dynamic melting viscosity of not more than 150 Pa·s, preferably less than 120 Pa·s and most desirably less than 80 Pa·s.

If at the desired processing temperature the dynamic viscosity of the internal-phase component is too low, a suitable softener such as glycerin may first have to be added. In some cases the active substance, Rotigotine, may itself have softening properties. This is the case for instance with polyvinyl pyrrolidone so that, when PVP is to be metered into an extruder, a PVP/Rotigotine premelt can be produced.

The internal-phase components are preferably selected out of the group of
(a) hydrophilic or amphiphilic polymers,
(b) hydrophilic or amphiphilic copolymers,
(c) mixtures of (a) and/or (b) with pharmaceutically acceptable softeners,
(d) condensates from glycerin with fatty acids or polyols,
(e) suitable mixtures of the substances (a)-(d).

Internal-phase components suitable for use in the TTS per this invention may be selected for instance from the group of polysaccharides, substituted polysaccharides, polyethylene oxides, polyvinyl acetates, polyvinyl pyrrolidones (PVP), PVPs with suitable softeners, polyethylene glycols, polypropylene glycols, acrylates, copolymers from polyvinyl pyrrolidone and (poly)vinyl acetate, copolymers from ethylene and vinyl acetate, as well as polyvinyl alcohols with a suitable softener such as glycerin.

The preferred internal-phase components are PVP, PVP with softener, polyethylene oxides (PEO), polyvinyl acetates (PVA), and copolymers from PVP and vinyl acetate.

The internal-phase component is added to the adhesive layer at a concentration of 0-40 weight % as related to the overall weight of the adhesive layer, with the preferred amount of the added internal-phase component being 2-25 weight %.

A surprising discovery was made whereby, given a constant amount of the active substance and perhaps a softener, the internal-phase component not only promotes the solubility of the Rotigotine and thus its uniform distribution in the matrix but, as the quantity is increased, it can also lead to a retardation i.e. linearization of the Rotigotine release.

Using the example of a silicone-based hot-melt TTS, FIGS. 5a and 5b show the effect of the PVP content on the in-vitro Rotigotine permeation through murine skin. As the PVP content is increased, it leads to a linearization of the Rotigotine permeation rate (FIG. 5a) that is attributable to a significant reduction of the initial release of the active substance (FIG. 5b). FIG. 5c shows the effect of different PEO concentrations on the permeation of Rotigotine from a silicone-based hot-melt TTS through human skin.

This retardation effect of the internal-phase component can be utilized for instance in the case of hot-melt TTSs with a high active-substance charge for producing a patch that releases the active substance, Rotigotine, in uniform, therapeutically effective quantities over an extended period such as at least 3 days, or at least 4, 5, 6 or 7 days.

Assuming an average daily dose of 6 mg Rotigotine, the necessary hourly steady-state Rotigotine flux rate will be 250 μg. For a TTS with a surface area of between 10 and 30 cm² that means a necessary flux rate of 8.3-25 μg/cm²/h.

In in-vitro permeation experiments on human skin with the disclosed silicone-based hot-melt TTS having a Rotigotine charge of about 23-25 weight % and a patch weight of 54-84 g/m², i.e. a Rotigotine content of 1.2-2.1 mg/cm² of matrix, it was possible to achieve continuous flux rates of 12-16 μg/cm²/h over a period of at least 3 days (see FIG. 6a).

That flux rate was on the order of magnitude of the clinically relevant flux rate obtained with the comparative silicone-based TTS produced by the solvent method. After about 48 hours, with the active-substance supply exhausted, the permeation curve of the comparative TTS broke off while the supply of the more highly charged hot-melt TTS was not exhausted even after 72 hours.

Applying the hot-melt TTS according to this invention on a human skin model as described in Implementation Example #9, a Rotigotine concentration of 25 weight % and a matrix weight of 85 g/m² made it possible, after an initial lag phase, to maintain a 7-day steady-state flux rate through the human skin of about 15 μg/cm²/h (FIG. 6b). That result was confirmed in another test in which wax types ceresine and ozokerite performed equally well (FIG. 6c).

Therefore, one object of this invention is a TTS whose adhesive matrix contains Rotigotine or a Rotigotine prodrug as the active substance in an amount of at least 20 weight %, and preferably over 25 weight %, and which, in an in-vitro permeation test on human skin as described in Implementation Example #9, leads to a continuous flux rate of at least 8 µg/cm²/h, or preferably 10 µg/cm²/h, lasting over a period of at least 5, 6 or 7 days.

Another object of this invention is a hot-melt TTS that contains Rotigotine as the active substance in its adhesive layer in an amount of at least 20 weight % and preferably at least 25 weight % and which, in an in-vitro permeation test on human skin as described in Implementation Example #9, attains a continuous flux rate of at least 8 µg/cm²/h for a period of at least 7 days.

For the first time, a TTS is provided that is capable of administering Rotigotine through mammalian and especially human skin at an hourly flux rate of 200-300 µg over a period of 5, 6 or 7 days.

Therefore, one aspect of this invention is a TTS, preferably a hot-melt TTS and especially a silicone-based hot-melt TTS, that lends itself to the continuous administration of Rotigotine over a period of at least 5, 6 or 7 days at a steady-state flux rate of 200-300 µg/day.

For the purpose of this patent application, the term "steady state" refers to a flux equilibrium that establishes itself following an initial lag phase after a first application of the novel product.

The term "steady-state flux rate" refers to a flux rate in a flux equilibrium that establishes itself after the initial lag phase.

In a preferred implementation of this invention, the flux rates stated in the patent application are constant flux rates.

For the purpose of this patent application, the term "constant flux rate" refers to a steady-state flux rate at which Rotigotine is transported through the human skin at an average flux rate with an intraindividual variability CV, over time, of not more than 30%, preferably of not more than 20% or even of not more than 10%, where CV is determined by the equation $CV=(sd: x) \times 100\%$ (ref. calculation by Cawello (ED) in "Parameters for Compartment-free Pharmacokinetics", Shaker Verlag Aachen, 1999, page 112). A daily dose is administered at an average flux rate of daily dose divided by 24 (mg/hour) with a CV of 30%. Those skilled in the art realize that a constant flux rate does not establish itself until an initial lag phase following the first application of the product. Hence, the lag phase is ignored in calculating the constant flux.

Another object of this patent application is a TTS for the transdermal administration of Rotigotine, encompassing an active-substance-containing layer, characterized in that:
(a) the active-substance-containing layer
  (a1) incorporates a Rotigotine component of at least 20 weight % and preferably at least 25 weight %,
  (a2) has a Rotigotine concentration of at least 2.0 mg/cm², preferably 2.8 mg/cm² and most desirably at least 3.1 mg/cm² or at least 3.4 mg/cm²,
  (a3) optionally contains an amount of an active-substance-retardant organic wax and/or an internal-phase component, and
(b) upon application of the TTS on the patient's skin, will transcutaneously dispense Rotigotine over a period of at least 5 days and preferably at least 7 days at a steady-state flux rate of 100-500 µg/hour and preferably 200-300 µg/hour.

Another object of the invention is a Rotigotine-containing TTS, preferably a Rotigotine-containing hot-melt TTS and, most desirably, a Rotigotine-containing silicone-based hot-melt TTS, characterized in that:
(a) the Rotigotine is contained in the adhesive matrix in an amount of at least 20 weight % and preferably at least 25 weight %,
(b) the adhesive matrix has a Rotigotine content of at least 2.0 mg/cm², preferably 2.8 mg/cm² and most desirably at least 3.1 mg/cm² or at least 3.4 mg/cm², and
(c) Rotigotine is released to the patient over a period of at least 5, 6 or 7 days at a steady-state rate of at least 100-500 µg/hour, preferably 200-300 µg/hour and most desirably 230-270 µg/hour.

For standardizing the solvent-based, Rotigotine-containing silicone TTS, the in-vitro model per Tanojo (J Contr. Release 45 (1997) 41-47), used for measuring the flux rate through the human skin, has proved to be a good model for predicting the in-vivo flux rate determined in clinical studies. In contrast to a few other in-vitro human-skin models employed for comparison purposes, the flux rates through the human skin as determined by the Tanojo model correlated excellently with the results obtained in clinical studies (Phase III) in terms of flux rates, plasma levels and clinical parameters such as the UPDRS score.

The results obtained with the model described in Implementation Example #9 therefore suggest that the hot-melt TTS is equally suitable for the in-vivo administration of Rotigotine in therapeutically effective amounts over a period of several days.

In clinical practice, the flux is preferably set at a rate where the patient maintains a continuous therapeutic plasma level of between 0.4 and 2 ng/mL of blood. This requires an hourly Rotigotine flux through the patient's skin of 100-400 µg, preferably about 200-300 µg (corresponding to 10-15 µg/cm²/h for a 20 cm² TTS), desirably 230-270 µg and ideally about 250 µg. The standard dosage may be varied especially in adaptation to the patient's physical constitution. As shown in FIG. 6b, this flux rate is achievable over a 7-day period employing the TTS according to the invention.

Thus, for the first time, a TTS for the continuous transdermal administration of Rotigotine is provided which, when applied on human skin, induces an average plasma concentration of 0.4-2 ng/ml Rotigotine over a period of at least 5, 6 or 7 days.

Another aspect of this invention is a TTS, preferably a hot-melt TTS and especially a silicone-based hot-melt TTS, that lends itself to the continuous administration of Rotigotine to humans over a period of at least 5, 6 or 7 days, where over at least 80%, preferably at least 90% and most desirably at least 95% of the time selected the plasma level in the patient's circulatory system is set at between 0.4 and 2 ng Rotigotine per mL of blood.

The above statements also apply to TTSs per this invention which contain Rotigotine prodrugs such as an ester or carbamate. After an appropriate amount of the prodrug has been administered, the Rotigotine is released in the skin and/or blood by cleavage of the prodrug.

Those skilled in the art are familiar with other additives that may in principle be contained in the adhesive layer, such as antioxidants, stabilizers, tackifiers, preservatives or permeation enhancers. Whether the addition of such substances to the essential components per this invention, as defined in the claims, is useful in any given case can be determined by routine tests and such implementations are therefore specifically made a part of this invention.

In one preferred form of implementation of the invention the disclosed hot-melt TTSs do not contain any permeation enhancers.

One form of implementation of the invention is therefore a hot-melt TTS encompassing a adhesive matrix that contains:
(a) 50-99 weight % of a hot-meltable adhesive (b) 1-40 weight %, preferably 5-30 weight %, desirably 9-30 weight % and ideally 15-25 or 20-30 weight % of Rotigotine.
(c) 040 weight %, preferably 2-25 weight % and most desirably 5-25 weight % of an internal-phase component preferably selected from among the group of polysaccharides, substituted polysaccharides, polyethylene oxides, polyvinyl acetates, polyvinyl pyrrolidones with or without softeners, polyethylene glycols, polypropylene glycols, acrylates, copolymers from polyvinyl pyrrolidone and (poly) vinyl acetate, copolymers from ethylene and vinyl acetate, as well as polyvinyl alcohols with a softener such as glycerin;
(d) 0-10 weight %, preferably 0-5 weight % and most desirably 0-3% of other additives such as tackifiers, antioxidants, stabilizers, permeation enhancers,
  where the hot-meltable adhesive (a) is preferably a mixture of (i) 70-99 weight % of an amine-resistant silicone adhesive
  (ii) 1-30 weight % of a suitable softener, especially a wax, preferably an organic wax and most desirably ozokerite or ceresine.

The hot-melt TTS may consist exclusively of the adhesive matrix, but in addition to the Rotigotine-containing adhesive matrix it preferably includes such components as a backing (2) that is impermeable to the active substance and inert to the components of the adhesive matrix, and a protective foil (3) that covers the adhesive matrix (1) and must be removed before use (see FIG. 10). Those skilled in the art are familiar with other possible variations of the TTS configuration, including for instance an added membrane that controls the flux of the active substance, and/or an added adhesive foil ("overtape"). Particular preference is given to the "monolithic" TTS configuration depicted in FIG. 10.

Rotigotine is a dopamine agonist. Therefore, the TTS according to the invention is especially suitable for the treatment of diseases associated with dopamine-metabolic disorders, most particularly Parkinson's disease or Restless Leg syndrome.

One object of the invention, therefore, is a method for treating dopamine-metabolic diseases, especially Parkinson's disease or Restless Leg syndrome, characterized in that a Rotigotine-containing hot-melt TTS according to this invention is applied on the skin of a patient.

Another object of the invention is a product package holding one or several Rotigotine-containing hot-melt TTSs per this invention as well as instructions for their use.

So far, the only methods known from prior art for the production of Rotigotine-containing TTSs have employed a solvent-based Rotigotine-containing adhesive matrix, requiring the removal of the solvent from a solvent-containing silicone- or acrylate-based dispersion. This present invention is the first to introduce a solvent-free hot-melt method for producing a Rotigotine-containing TTS.

Therefore, one aspect of this invention is a method for producing a TTS encompassing a adhesive matrix that contains Rotigotine as the active substance, characterized in that, prior to being laminated onto a foil, the components of the adhesive matrix are melted and homogenized, solvent-free, at temperatures of between 70 and 200° C., preferably between 100 and 200° C. and most desirably between 120 and 160° C. The ideal operating temperature in the extruder is between 130 and 150° C.

Surprisingly, it was found that, after the melting, the Rotigotine remains stable in a variety of matrices even without the addition of stabilizers or antioxidants. HPLC measurements with UV analyses at 220 nm and 272 nm have shown that even without the admixture of antioxidants the purity level of the active substance routinely remained above 98% and generally better than 99% (Table 2-4; Implementation Examples #4, 6, 7).

Therefore, one aspect of the invention is the use of Rotigotine in the production of a TTS, characterized in that the Rotigotine is infused in the adhesive layer of the TTS by the hot-melt method.

It is generally possible to introduce the Rotigotine in the matrix either premelted or by metering it in solid form into the hot matrix melt where it is melted.

In a preferred form of implementation the Rotigotine is melted at temperatures between 100 and 200° C., preferably between 120 and 160° C. and desirably between 130° C. and 150° C., in that Rotigotine in its solid state is metered into the molten matrix, optionally without the addition of stabilizers or antioxidants.

In a particularly preferred form of implementation the Rotigotine is melted by metering it, in its solid state, into the hot molten matrix and by briefly homogenizing and then calendering the Rotigotine-containing matrix melt onto a foil substrate where it is cooled. In that operation the Rotigotine is exposed, preferably for a maximum of 5 minutes and most desirably for less than 4, 3, 2 or even 1 minute(s), to a temperature of 100° C. to 200° C., preferably 120-160° C. and ideally 130-150° C.

Another aspect of this invention is, therefore, the use of Rotigotine for producing a TTS by the hot-melt method at temperatures of between 120 and 160° C. and most preferably at 130° C. to 150° C., whereby the hot-melt process produces a adhesive matrix containing Rotigotine at a purity level of at least 98% and preferably 99% as measured at 220 and 272 nm.

In another form of implementation of the invention, the adhesive layer of the TTS is melted at very low temperatures of 70-75° C., which is just below the melting point of Rotigotine. That leaves the Rotigotine in the matrix in its solid state. This method requires the use of hot-meltable adhesives that permit processing at 70° C., while on the other hand the dynamic viscosity of the adhesive mixture must not be set too low to avoid cold flux of the adhesive layer on the skin. The process therefore requires the application of a fairly high shearing force.

Therefore, one aspect of this invention is the production of a TTS by the hot-melt method, whereby the adhesive layer is melted at temperatures below the melting point of Rotigotine, meaning below about 75° C., and the Rotigotine in its solid state is metered into the melt.

For the industrial production of the TTS the adhesive layer is preferably prepared in an extruder. In that process, the individual components of the adhesive layer can be introduced in the extruder, for instance a dual-screw extruding machine, via the respective feed channels either separately or in premixed form. The resulting mixture is mixed in the extruder under controlled heating conditions, whereupon it can be continually processed and ultimately laminated.

Since at room temperature the hot-meltable adhesive remains solid, premelting is necessary. That can be accomplished for instance by means of a melting/metering system consisting of a container with controlled heating, in which the hot-meltable adhesive such as the hot-meltable silicone adhesive is premelted at temperatures between 70° C. and 200° C., preferably between 100° C. and 170° C., desirably between 120° C. and 160° C. and ideally between 130 and 150° C. The melting/metering system permits continuous feeding, allowing it to be easily integrated into the continuous production system. The metering section may be of the volumetric or gravimetric type.

In hydrophobic adhesives such as silicones, Rotigotine is soluble in trace amounts only, which is why it must be dispersed. The viscosity of the molten Rotigotine is very low, as a result of which there may be considerable viscosity differences during the process between the adhesive and the active substance. For optimizing the distribution of the active substance in the adhesive matrix, one has the option of integrating static mixing agents in the extrusion process to ensure an even more homogeneous blending of the adhesive matrix. Suitable static mixing agents are available for instance from Sulzer Chemtech GmbH. It has thus been possible, as verified by microscope analyses of the adhesive matrix, to reduce the droplet size of the active-substance particles and of the internal-phase domains to an average of less than 20 µm.

There are several advantages to that:

For one, it prevents the formation of larger active-substance particles in the matrix that might lead to an uneven flux, to an adhesion/cohesion imbalance or to the recrystallization of the active substance.

For another, it prevents the accumulation of the active substance at the interface between the adhesive matrix and the skin that could cause skin irritation and/or protonation of the active substance with the consequent reduction of the flux rate through rediffusion of the protonized base.

Therefore, the size of the active microparticles should not exceed 80%, preferably 60% or ideally 50% of the thickness of the adhesive matrix. The average size of these microparticles is preferably in a range up to 40% and desirably up to 30% of the matrix thickness.

Assuming a matrix thickness for instance of 50 µm, the internal phase in the adhesive matrix would then preferably be in the form of droplets with an average size of up to 20 µm and preferably up to a maximum of 15 µm.

FIG. 8 shows the in-vitro permeation of Rotigotine through murine skin from different silicone-based hot-melt TTSs produced by fused extrusion in an extruder under utilization of different internal-phase components.

Apart from the silicone-based adhesive systems, other hot-meltable adhesives are in principle equally suitable for use in the Rotigotine-containing hot-melt TTSs according to this invention.

Hot-meltable adhesives have been described in prior art. Examples of usable types include hot-meltable adhesives based on styrene block copolymers ("SXS adhesives") derived from polymers with non-elastomeric styrene blocks at the ends and elastomer blocks in the middle. The elastomer blocks may consist for instance of polyethylene butyl, polyethylene propylene, polybutadiene or polyisopropene.

Adhesives of that type have been described for instance in U.S. Pat. Nos. 5,559,165 and 5,527,536. They offer good adhesive properties, are easy to produce and process and are well tolerated on the skin. SXS adhesives can be procured commercially (e.g. as Duro Tak 378-3500 from National Starch & Chemical), or they can be produced using hot-melt extrusion equipment in the course of the production of the active-substance-containing patches. This involves the individual metering into and mixing and melting in the extruder of corresponding quantities (at least of the following components) of a styrene block copolymer (such as Shell Kraton GX1657 or Kraton D-1107CU) with a resin (such as Keyser-Mackay Regalite R1090 or Regalite R1010 or Regalite R1100) and an oil (such as Shell Ondina 933 or Ondina 941). As the last step, the active substance is metered into the adhesive thus produced in the extruder and the compound is then laminated onto a foil. Examples of typical polymer/resin/oil weight ratios are 100/120/20 or 100/200/50. By varying these ratios it is possible to adapt the properties of the SXS adhesive to the respectively desired properties of the TTS (adhesive strength, minimal cold flux, adhesive duration, release pattern of the active substance, etc.).

Because of the oxidative effect of the SXS adhesives a preferred method is to add antioxidants to such SXS-based adhesive matrices. One example of a commercially available, suitable antioxidant is Irganox® (by CIBA).

Another example consists in hot-meltable adhesives that are based on ethylene vinyl acetate copolymers ("EVA adhesives"). EVA adhesives of that type are described for instance in U.S. Pat. No. 4,144,317. EVA adhesives offer good adhesive properties, they are easy to produce and process and are well tolerated on the skin. They are available for instance from Beardow Adams (13/BA).

It was possible both with hot-meltable SXS-type adhesives and with hot-meltable EVA-type adhesives to produce Rotigotine-containing TTSs that encompassed hot-melt adhesive matrices and released the Rotigotine in proper amounts (FIG. 7).

FIGS. 9 and 9a shows the in-vitro permeation, through murine skin, of Rotigotine from EVA-based hot-melt TTSs with varying Rotigotine contents, produced by fused extrusion in an extruder.

Therefore, one object of this invention is a transdermal therapeutic system (TTS) encompassing a Rotigotine-containing adhesive matrix, characterized in that the adhesive matrix contains a hot-meltable adhesive in which the active substance, Rotigotine, ((−)-5,6,7,8-tetrahydro-6-[propyl[2-(2-thienyl)ethyl)amino]-1-napththol), is dispersed and partly or completely dissolved, said hot-meltable adhesive being of the SXS-type or EVA-type.

One form of implementation of this invention is thus represented by a hot-melt TTS that comprises a adhesive matrix containing:
(a) 50-99 weight % of a hot-meltable adhesive,
(b) 140 weight %, preferably 5-30 weight %, desirably 9-30 weight % and ideally 15-25 weight % Rotigotine or a Rotigotine prodrug,
(c) 040 weight %, preferably 2-25 weight % and desirably 5-25 weight % of an internal-phase component preferably selected from the group of polysaccharides, substituted polysaccharides, polyethylene oxides, polyvinyl acetates, polyvinyl pyrrolidones with or without softeners, polyethylene glycols, polypropylene glycols, acrylates, copolymers from polyvinyl pyrrolidone and (poly)vinyl acetate, copolymers from ethylene and vinyl acetate, as well as polyvinyl alcohols with a softener such as glycerin, plus
(d) 0-10 weight %, preferably 0-5% and most desirably 0-3% of other additives such as tackifiers, antioxidants, stabilizers and/or permeation enhancers,
with the hot-meltable adhesive per (a) being preferably selected from
(a1) an EVA adhesive,
(a2) an SxS adhesive, or
(a3) a mixture consisting of
  (i) 70-99 weight % of an amine-resistant silicone adhesive,
  (ii) 1-30 weight %, preferably 3-15 weight % and ideally 4-10 weight % of a suitable softener, preferably an organic wax—most desirably ceresine or ozokerite,
where, optionally, softeners may be added to the EVA adhesive (a1) and to the SXS adhesive (a2) and, if an SXS adhesive is used, an antioxidant is added.

If an individually hot-meltable adhesive for instance of the SXS type or of the EVA type is to be adapted to specific processing requirements, it is again possible, as an option, to add other substances to the composition, such as softeners, tackifiers, antioxidants, amphiphilic polymers etc.

A comparison of the release pattern of Rotigotine from the various hot-melt adhesives revealed that the TTS with the silicone-based hot-melt adhesive is the most efficacious. With the SXS-based and EVA-based hot-melt TTS, the Rotigotine release drops off to a level that is no longer therapeutically effective at a point where about 30 weight % of the Rotigotine is still present in the adhesive matrix. By contrast, the silicone-based hot-melt TTS allowed nearly total depletion.

Therefore, a Rotigotine-containing hot-melt TTS produced with a silicone-based hot-melt adhesive as described above is given particular preference.

EXPERIMENTS

Comparative Reference Example

Solvent-based Silicone TTS 1.8 g of (free-base) Rotigotine was dissolved in 2.4 g ethanol and added to 0.4 g Collidone 90 F (dissolved in 1 g ethanol). The resulting mixture was added to a 74% solution of silicone polymers (8.9 g BioPSA 7-4201+8.9 g BIO-PSA 7-4301 [Dow Corning]) in heptane. After adding 2.65 g petroleum ether the mixture was agitated for 1 hour at 700 RPM to produce a homogeneous dispersion. After lamination onto polyester it was dried at 50° C. The final weight of the patch was 50 g/cm².

1st Example

Silicone-Based Hot-melt TTS with 15% Rotigotine Produced in Lab Quantities (a) Silicone Hot-melt Adhesive The silicone-based hot-melt adhesives employed contained the Bio-PSA 7-4300 silicone adhesive (Dow Corning, Michigan) mixed with ozokerite or ceresine softeners at 5%, 10% or 15% of the overall weight of the adhesive mixture (purchased from Dow Corning).

(b) Producing the TTS 8.5 g of a silicone-based adhesive mixture as described in (a) was heated to 160° C. over about 20 minutes until a homogeneous melt was obtained. 1.5 g (free-base) Rotigotine was added and the mixture was kept at 160° C. for another 5 minutes. The mixture was then manually homogenized and laminated onto a preheated foil (120° C., gap width 250 μm). 5 cm² sections were then cut out.

2nd Example

Producing a Silicone-Based Hot-melt TTS with an Internal Phase

This was produced as in Example #1, with 0.5 g of an internal-phase component added together with the Rotigotine.

3rd Example

Producing a Silicone-Based Hot-melt TTS in Lab Quantities with Varied Parameters The TTSs were in all cases produced as in Examples # 1 and #2, while the different parameters such as the type of wax, the wax content, the concentration of the internal-phase component, the active-substance content and the patch density were varied as follows:

TABLE 1

| | Silicone-based Hot-melt TTS | | | | | |
|---|---|---|---|---|---|---|
| Lot No. | Ceresine Content [% w/w] | Ozokerite Content [% w/w] | Internal Phase Type & Content [% w/w] | Theoret. Rotigotine Content [% w/w] | Actual Rotigotine Content (n = 5) [% w/w] | Weight of Adhesive Matrix (n = 10) [g/m²] |
| 20011031 | 15 | — | PVP/10 | 9 | 8.51 | 108 |
| 20011032 | 15 | — | PVP/2 | 9 | 9.23 | 83 |
| 20011035 | 15 | — | PVP/2 | 15 | 15.81 | 66 |
| 20011036 | 15 | — | PVP/10 | 15 | 15.56 | 100 |
| 20012038 | 15 | — | PVP/2 | 9 | n.d. | 123 |
| 20012040 | 15 | — | PVP/2 | 15 | n.d. | 118 |
| 20012042 | 15 | — | PVP/2 | 25 | n.d. | 114 |
| 20103042 | 15 | — | 0 | 15 | 15.25 | 57 |
| 20103043 | 15 | — | PVP/25 | 15 | 14.04 | 127 |
| 20105038 | 15 | — | 0 | 9 | 8.75 | 91 |
| 20105039 | 15 | — | PVP/2 | 9 | 9.07 | 88 |
| 20105040 | 15 | — | PVP/10 | 9 | 9.14 | 91 |
| 20105041 | 5 | — | 0 | 9 | 8.08 | 106 |
| 20105043 | — | 5 | 0 | 9 | 8.03 | 105 |
| 20105044 | 15 | — | 0 | 15 | 14.50 | 78 |
| 20105045 | 15 | — | 0 | 25 | 25.20 | 77 |
| 20106016 | — | 15 | 0 | 9 | 8.12 | 88 |
| 20107040 | — | 5 | 0 | 15 | 13.71 | 99 |
| 20107041 | — | 5 | 0 | 25 | 24.71 | 84 |
| 20109009 | — | 15 | 0 | 15 | 13.28 | 89 |
| 20109010 | 5 | — | 0 | 15 | 14.09 | 107 |
| 20111059 | — | 5 | 0 | 25 | 23.95 | 54 |
| 20111058 | — | 5 | 0 | 15 | 14.57 | 54 |
| 20111057 | — | 5 | 0 | 9 | 8.64 | 56 |
| 20109043 | — | 5 | 0 | 25 | 22.69 | 117 |
| 20105044 | — | 15 | 0 | 15 | 14.49 | 57 |

TABLE 1-continued

Silicone-based Hot-melt TTS

| Lot No. | Ceresine Content [% w/w] | Ozokerite Content [% w/w] | Internal Phase Type & Content [% w/w] | Theoret. Rotigotine Content [% w/w] | Actual Rotigotine Content (n = 5) [% w/w] | Weight of Adhesive Matrix (n = 10) [g/m²] |
|---|---|---|---|---|---|---|
| 20103043 | — | 15 | 0 | 15 | 14.04 | 78 |
| WE11682*) | — | — | PVP/2 | 9 | 8.83 | 50 |
| 20107011*) | — | — | PVP/2 | 9 | 9.90 | 110 |

*)Solvent-based comparative reference example;
PVP = polyvinyl pyrrolidone

The Rotigotine content and the weight of the adhesive matrix were determined as follows: 10 patches sized 5 cm², 10 cm² or 20 cm² were punched out and individually weighed, the weight was corrected by subtracting the average weight of the blank foils (measured by weighing sections of the same size, i.e. 5, 10 or 20 cm², respectively).

4$^{th}$ Example

Producing SXS- or EVA-based Hot-melt TTS in Lab Quantities 8.5 g of the SXS hot-melt adhesive (Duro-Tak 34-4230 by National Starch & Chemical) or 8.5 g of the EVA hot-melt adhesive was heated at 160° C. for about 20 minutes until a homogeneous melt was obtained. 1.5 g or, respectively, 1.65 g of Rotigotine base was added and the mixture was manually homogenized. The mixture was then laminated onto a preheated chill roll (120° C.). 5 cm² patches (for permeation experiments) and 20 cm² patches (for determining the patch weight) were then cut out. The matrix weight is shown in Table 2 below.

5$^{th}$ Example

Producing a Silicone-based Hot-melt TTS with 15% Rotigotine and 5% Internal Phase in an Extruder A. Producing a Premelt of the Silicone-adhesive Mixture The desired amount of the silicone-adhesive mixture as described in Example #1 was preheated to 140° C. and placed in a metering unit (Meltex GR 12-1 by Melzer). The mixture was then volumetrically metered into the extruder.

B. Producing the Adhesive Matrix by the Hot-melt Method

A dual-screw extruder (25×24D by Dr. Collin GmbH) was used for small to moderate production quantities and a dual-screw extruder (ZSK25 by Werner Pfleiderer, Stuttgart) was used for large production quantities. The process conditions were 5 kg/h, with 120-140° C. heat zones. A Meizer CL200 was used for the laminating.

TABLE 2

| Lot No. | Adhesive | Internal-Phase Content [% w/w] | Theoretical Active-Substance Content [% w/w] | Actual Active-Substance Content [% w/w] | Weight (n = 10) [g/m²] | Purity % (220 nm/272 nm) |
|---|---|---|---|---|---|---|
| 20103041 | SXS | — | 15 | 14.96 | 85 | 94.9/94.3 |
| 20103048 | EVA | — | 16.2 | 18.24 | 58 | 98.1/99.7 |
| 20103047 | EVA | — | 16.2 | 15.96 | 127 | 98.8/99.9 |

6$^{th}$ Example

Producing a Silicone-based Hot-melt TTS in the Extruder with Varied Parameters

The TTS was in all cases produced as described in Example #5, with the parameters varied as follows:

TABLE 3

| No. | Lot No. | Scale | Static Mixing | Ceresine Content [% w/w] | Internal Phase Type & Content [% w/w] | Theoret. Rotigotine Content [% w/w] | Actual Rotigotine Content (n = 5) [% w/w] | Matrix Weight (n = 10) [g/m²] | Rotigotine Purity [%] (220 nm/272 nm) |
|---|---|---|---|---|---|---|---|---|---|
| 1 | 20105025 | large | − | 15 | PVA/10 | 9 | 8.88 | 117 | 99.3/99.7 |
| 2 | 20105025 | large | + | 15 | PVA/10 | 9 | 7.16*) | 117 | 99.3/99.9 |
| 3 | 20105018 | large | − | 15 | PVA/10 | 9 | 9.16 | 92 | 99.4/100 |
| 4 | 20105018 | large | + | 15 | PVA/10 | 9 | 8.36 | 86 | 99.5/100 |
| 5 | 20109006 | small | − | 15 | PVA/10 | 9 | 8.80 | 82 | 99.6 |
| 6 | 20109007 | small | − | 15 | PVPVA/10 | 9 | 8.96 | 98 | 98.3 |
| 7 | 20109008 | small | − | 15 | PEO/10 | 9 | 7.28 | 88 | 99.1 |

TABLE 3-continued

| No. | Lot No. | Scale | Static Mixing | Ceresine Content [% w/w] | Internal Phase Type & Content [% w/w] | Theoret. Rotigotine Content [% w/w] | Actual Rotigotine Content (n = 5) [% w/w] | Matrix Weight (n = 10) [g/m²] | Rotigotine Purity [%] (220 nm/272 nm) |
|---|---|---|---|---|---|---|---|---|---|
| 8 | 20108030 | small | + | 15 | — | 25 | 22.43 | 187 | 99.2/n.d. |
| 9 | 20105045 | small | − | 15 | — | 25 | 25.2 | 77 | 98.7/96.9 |

PVA = polyvinyl acetate;
PEO = polyethylene oxide
PVPVA = polyvinyl pyrrolidone-vinyl acetate copolymer

7th Example

Producing EVA-based Hot-Melt TTS in an Extruder

All TTSs were produced as described in Example #5, with the TTSs having the following compositions:

TABLE 4

| Lot No. | Scale | Internal-Phase Content [% w/w] | Theoretical Active-Substance Content [% w/w] | Actual Active-Substance Content (n = 5) [% w/w] | Weight (n = 10) [g/m²] | Rotigotine Purity [%] (220 nm/272 nm) |
|---|---|---|---|---|---|---|
| 20103048 | small | — | 16.2 | 18.24 | 58 | 98.1/99.7 |
| 20103047 | small | — | 16.2 | 15.96 | 127 | 98.8/99.9 |
| 20109019 | large | — | 9 | 8.62 | 93 | 98.9/99.9 |
| 20109045 | large | — | 15 | 15.08 | 104 | 99.4/n.d. |
| 20109020 | large | — | 20 | 18.57 | 89 | 96.1/n.d. |

8th Example

Determining the Flux of the Active Substance in the Murine-Skin Model

For measuring the flux through murine skin, abdominal and dorsal skin about 120 to 150 μm thick was used. A punched-out TTS with a surface area of 2.55 cm² in a horizontal diffusion cell was fastened to the keratic side of the abdominal and dorsal skin of hairless mice. Immediately thereafter the acceptor chamber of the cell was filled with a phosphate buffer solution (0.066 molar) preheated to 32° C., with a pH 6.2 and bubble-free, and the release medium was thermostatically controlled at 32±0.5° C.

At the time of the sampling the release medium was replaced with fresh medium thermostatically controlled at 32±0.5° C. The Rotigotine release was determined by HPLC as described in Example #10.

9th Example

Determining the Rotigotine Flux in the Human-Skin Model

The Rotigotine flux through human skin was essentially determined as described by H. Tanojo et al in J. Control Rel. 45 (1997) 41-47.

For that purpose, human skin about 250 μm thick was harvested from an abdomen. A TTS with a surface area of 2.545 cm² was applied on an identical area of the human skin, with the skin on the acceptor side resting on a silicone membrane (FIG. 11). The acceptor phase used was PBS (0.066 molar) at pH 6.2 and a temperature of 32±0.5° C. The experiments were conducted with a flux of 5 mL/h over 72 hours, with samples taken every 3 hours. At the time of the sampling the release medium was replaced with fresh medium thermostatically controlled at 32±0.5° C. and the amount of the released Rotigotine was measured by HPLC. The flux rate Q(t) relative to the surface of the measuring cell (0.552 cm²) was determined using this formula:

$$Q(t) = \mu g/cm^2 = \text{Rotigotine concentration times acceptor volume divided by } 0.552 \; cm^2$$

10th Example

Rotigotine Analytics (a) Analytics of The Active-substance Release

The flux of the active substance through the skin preparations was measured by HPLC (RPC18 LichroCART 754 Supersphere 60select column) under the following conditions: 650 parts by volume (VP) water, 350 VP acetonitrile, 0.5 VP methane sulfonic acid; room temperature; wavelength: 272 nm; flux 2 ml.

(b) Analytics of the Active Substance in the Matrix (b1) Preparing the Matrix

The adhesive matrix was mixed with 0.1% methane sulfonic acid, agitated, centrifuged and measured.

(b2) Analytics of the Active-substance Content

The active-substance content was determined by isocratic HPLC under the following conditions:

Solubilizer: 65 volume parts water with 0.05% methane sulfonic acid; 35 volume parts acetonitrile with 0.05% methane sulfonic acid.

Column: LiChroCART 75×4 mm, Supersphere 60 RP-select B 5 μm

Flow rate: 2 mL/min, column temperature: 30° C.

UV detection (272 nm)

(b3) Analytics of the Active-substance Stability:

The purity of the Rotigotine was determining by the gradient HPLC method with an aqueous and an organic (acetonitrile) phase, each with 0.05% methane sulfonic acid added. The organic component rose from the initial 5% to 60% over 35 minutes.

Column: LiChrosphere 100 CN, 125 mm×4.6 mm, 5 μm

Flow rate: 1.0 mL, column temperature: 40° C.

UV detection (2 wavelengths, 272 and 220 nm)

(b4) Determining the Dynamic Viscosity

The dynamic viscosity was determined as described in RE 36754.

The invention claimed is:

1. A transdermal therapeutic system comprising a drug-containing adhesive matrix, wherein the drug-containing adhesive matrix comprises:
   a solidified melt comprising rotigotine free-base present in an amount of 1-40 weight % with a purity level above 98% and
   a hot-melt adhesive present in an amount of 50-99 weight %,
   wherein the drug-containing adhesive matrix exhibits at 160° C. a dynamic viscosity of not more than 100 Pa·s and
   wherein the drug-containing adhesive matrix is produced by metering the rotigotine free-base into a solvent-free melt at a temperature of between 70° C. and 200° C.

2. The transdermal therapeutic system of claim 1 wherein the rotigotine free-base is dispersed or partly or completely dissolved in said hot-melt adhesive.

3. The transdermal therapeutic system of claim 1 wherein the metering of the rotigotine free-base into the solvent-free melt is at a temperature of between 120° C. and 160° C.

4. The transdermal therapeutic system of claim 1 wherein the hot-melt adhesive consists of a mixture of an amine-resistant silicone adhesive and at least one suitable softener.

5. The transdermal therapeutic system of claim 4 wherein the softener is an organic wax.

6. The transdermal therapeutic system of claim 4 wherein the softener is ceresine or ozokerite.

7. The transdermal therapeutic system of claim 1 wherein the proportion of rotigotine free-base in the adhesive layer is 4 to 40 weight %.

8. The transdermal therapeutic system of claim 1 wherein the proportion of rotigotine free-base in the adhesive layer is 9 to 30 weight %.

9. The transdermal therapeutic system of claim 1 wherein the proportion of rotigotine free-base in the adhesive layer is 20 to 40 weight %.

10. The transdermal therapeutic system of claim 1 wherein the drug-containing adhesive matrix additionally contains an internal-phase component selected from the group consisting of
    (a) hydrophilic and amphiphilic polymers;
    (b) hydrophilic and amphiphilic copolymers;
    (c) mixtures of (a) and/or (b) with pharmaceutically acceptable softeners;
    (d) condensates from glycerin and fatty acids or polyols; and
    (e) suitable mixtures of the components (a)-(d).

11. The transdermal therapeutic system of claim 10 wherein the internal-phase component is selected from the group consisting of polysaccharides, substituted polysaccharides, polyethylene oxides, polyvinyl acetates, polyvinyl pyrrolidones, copolymers from polyvinyl pyrrolidone and (poly)vinyl acetate, polyethylene glycol, polypropylene glycol, copolymers from ethylene and vinyl acetate, glycerin-fatty acid esters and mixtures of polyvinyl alcohol with glycerin.

12. (Withdrawn and Previously Presented) The transdermal therapeutic system of claim 1 wherein the adhesive matrix comprises:
    (a) 50-99 weight % of said hot-melt adhesive;
    (b) 4-40 weight % rotigotine in the base form;
    (c) 0-40 weight % of an internal-phase component; and
    (d) 0-10 weight % of other adjuvants.

13. The transdermal therapeutic system of claim 1 wherein the hot-melt adhesive is
    (a1) an EVA adhesive,
    (a2) an SxS adhesive, or
    (a3) a mixture of
        (i) 70-99 weight % of an amine-resistant silicone adhesive and
        (ii) 1-30 weight % of a suitable softener.

14. The transdermal therapeutic system of claim 1 comprising: a layer that comprises the rotigotine free-base, wherein the layer
    (a) contains the rotigotine free-base in a percentile proportion of 20-40 weight %,
    (b) has a rotigotine free-base content of at least 2.0 mg/cm$^2$, and
    (c) optionally contains an organic wax and/or internal-phase component in an amount sufficient to retard the release of the rotigotine free-base.

15. The transdermal therapeutic system of claim 14 wherein rotigotine is transported through the skin at a steady-state flux rate of 100-500 μg per hour over a period of at least 5 days.

16. The transdermal therapeutic system of claim 14 wherein rotigotine is transported through the human skin at a flux rate of 100-500μg per hour over a period of at least 7 days.

17. The transdermal therapeutic system of claim 14 wherein the system induces in the patient an average plasma concentration of 0.4 to 2 ng/ml rotigotine for a period of at least 5 days.

18. A method for producing the transdermal therapeutic system of claim 1, the method comprising: prior to lamination, components of the adhesive matrix are melted and homogenized, solvent-free, at temperatures of between 70° C. and 200° C.

19. The method of claim 18 wherein components of the adhesive matrix are melted and homogenized in an extruder.

20. The method of claim 18 wherein the hot-melting process takes place at temperatures between 120° C. and 160° C.

21. The method of claim 18 wherein the rotigotine free-base is introduced, in the adhesive matrix melt, in its solid state.

22. The method of claim 18 wherein the adhesive matrix, produced by the hot-melting process, contains the rotigotine free-base at a purity level of at least 98% as measured by HPLC at 220 nm and 272 nm.

* * * * *